United States Patent [19]
Castor et al.

[11] Patent Number: 5,776,486
[45] Date of Patent: *Jul. 7, 1998

[54] METHODS AND APPARATUS FOR MAKING LIPOSOMES CONTAINING HYDROPHOBIC DRUGS

[75] Inventors: Trevor P. Castor, Arlington; Ling Chu, Chelmsford, both of Mass.

[73] Assignee: Aphios Corporation, Woburn, Mass.

[*] Notice: The term of this patent shall not extend beyond the expiration date of Pat. No. 5,554,382.

[21] Appl. No.: 631,808

[22] Filed: Apr. 12, 1996

Related U.S. Application Data

[63] Continuation-in-part of Ser. No. 342,443, Nov. 18, 1994, abandoned, which is a continuation-in-part of Ser. No. 69,134, May 28, 1993, Pat. No. 5,554,382.

[51] Int. Cl.⁶ .................................................. A61K 9/127
[52] U.S. Cl. .......................... 424/450; 264/4.1; 264/4.3; 264/4.6
[58] Field of Search ........................... 424/450; 264/4.1, 264/4.3, 4.6; 436/829

[56] References Cited

U.S. PATENT DOCUMENTS

| | | |
|---|---|---|
| 4,608,211 | 8/1986 | Handjani ................................. 264/4.6 |
| 4,971,803 | 11/1990 | Li .......................................... 424/450 |
| 5,399,694 | 3/1995 | Riess ...................................... 546/2 |

*Primary Examiner*—Gollamudi S. Kishore

[57] ABSTRACT

The present application features methods and apparatus for making liposomes containing hydrophobic drugs, with critical, supercritical or near critical fluids. The methods and apparatus combine a phospholipid, a drug, and an aqueous phase, or multilamellar vesicles, with a critical, supercritical or near critical fluid. Upon a reduction in pressure, liposomes are formed.

31 Claims, 19 Drawing Sheets

CONCENTRATION PROFILE OF PACLITAXEL AND CEPHALOMANNINE IN ELUTED LIPOSOMAL SOLUTION FROM GEC COLUMN. LIPOSOMES ARE PREPARED BY THE CRITICAL FLUID PROCESS (LIP-154).

Fig. 8  AN HPLC CHROMATOGRAM OF CAMPTOTHECIN AT A CONCENTRATION OF 0.04 mg/ml

CONCENTRATION PROFILE OF PACLITAXEL AND CEPHALOMANNINE IN ELUTED LIPOSOMAL SOLUTION FROM GEC COLUMN. LIPOSOMES ARE PREPARED BY THE CRITICAL FLUID PROCESS (LIP-154).

LIPOSOME SIZE AND INTENSITY DISTRIBUTION FROM GEC COLUMN. LIPOSOMES ARE PREPARED BY THE SONICATION METHOD (LIP-166).

CONCENTRATION PROFILE OF PACLITAXEL AND CEPHALOMANNINE IN ELUTED LIPOSOMAL SOLUTION FROM GEC COLUMN. LIPOSOMES ARE PREPARED BY THE SONICATION METHOD (LIP-166).

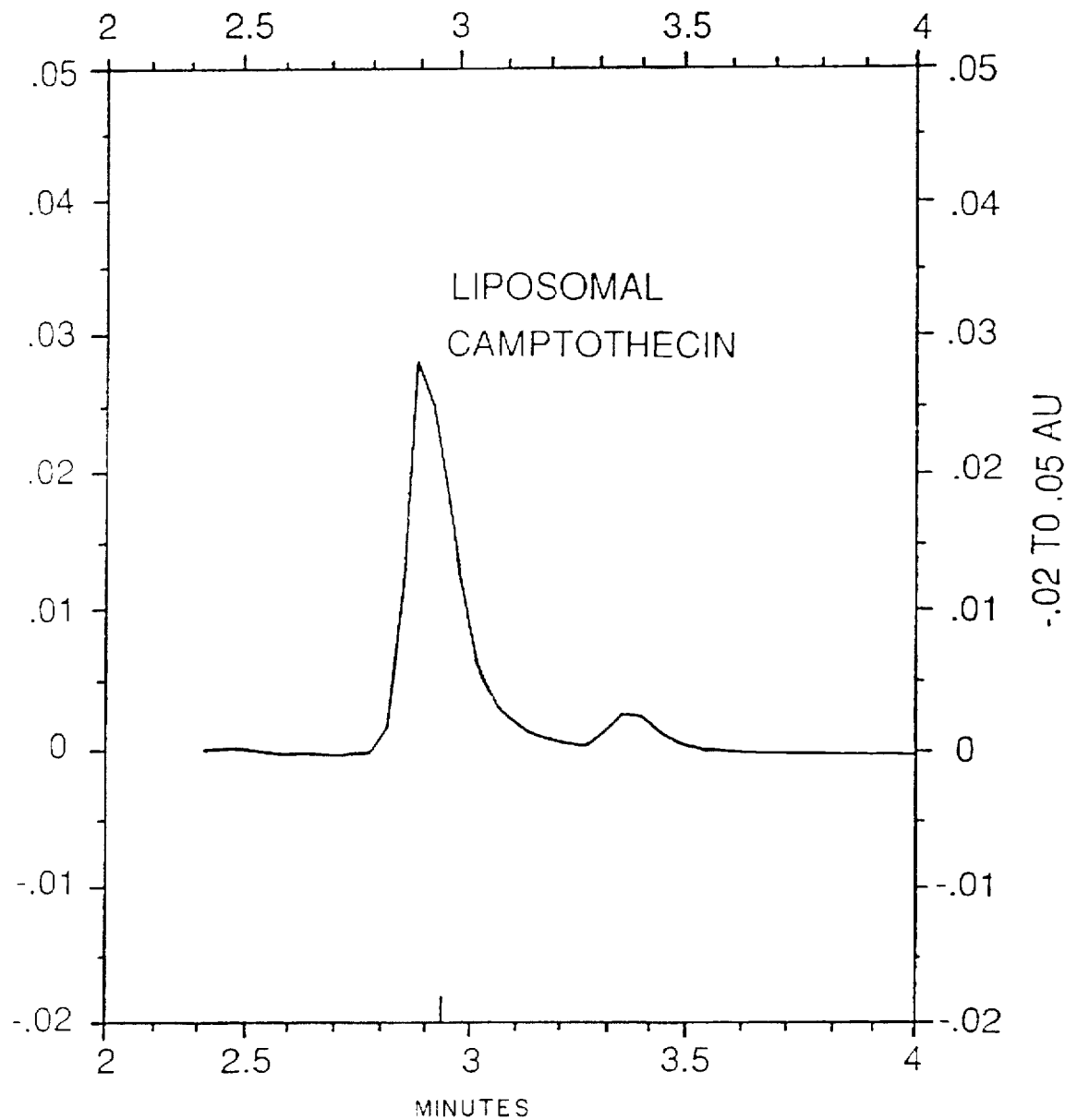
Fig. 13 AN HPLC CHROMATOGRAM OF LIPOSOMAL ENCAPSULATED CAMPTOTHECIN

TOXICITY TEST OF CRITICAL FLUID LIPOSOMES WITHOUT PACLITAXEL (LP-171)

TOXICITY TEST OF LIPOSOMAL ENCAPSULATED PACLITAXEL, SURVIVAL AS A FUNCTION OF DOSAGE LEVEL (LIP-176).

TOXICITY TEST OF PACLITAXEL SAMPLE. PERCENT CELL SURVIVAL AS A FUNCTION OF DOSAGE LEVEL.

METHODS AND APPARATUS FOR MAKING LIPOSOMES CONTAINING HYDROPHOBIC DRUGS

This application is a continuation-in-part of a U.S. patent application Ser. No. 08/342,443, filed Nov. 18, 1994, entitled METHODS AND APPARATUS FOR MAKING LIPOSOMES CONTAINING HYDROPHOBIC DRUGS, now abn., which is a continuation in part of U.S. patent application Ser. No. 08/069,134, filed May 28, 1993, entitled METHODS AND APPARATUS FOR MAKING LIPOSOMES now U.S. Pat. No. 5,554,382.

FIELD OF INVENTION

This invention relates generally to methods and apparatus for making liposomes which liposomes contain hydrophobic drugs. Examples of hydrophobic drugs comprise taxoids, camptothecins, doxorubicin, michellamine B, vincristine, bryostatin-1, halomon, and cisplatin. The methods and apparatus feature critical, supercritical, or near critical fluids.

BACKGROUND OF THE INVENTION

Liposomes are microscopic vesicles having single or multiple phospholipid bilayers which can entrap hydrophilic compounds within their aqueous cores. Hydrophilic compounds may partition into the phospholipid bilayers. Liposomes have been formed in sizes as small as tens of Angstroms to as large as a few microns. Most liposomes are non-toxic, non-antigenic and biodegradable in character since they have the molecular characteristics of mammalian membranes.

Liposomes are used as carriers for drugs. Liposomes can be made with different features which can enhance a drug's efficacy; reduce a drug's toxicity; and prolong the drug's therapeutic effect.

Liposomes with multiple bilayers are known as multilamellar vesicles (MLVs). MLVs are excellent candidates for time release drugs because the fluids entrapped between layers are only released as each membrane degrades. Liposomes with a single bilayer are known as unilamellar vesicles (UV). UVs may be made extremely small (SUVs) or large (LUVs).

Liposomes are prepared in the laboratory by sonication, detergent dialysis, ethanol injection, French press extrusion, ether infusion, and reverse phase evaporation. These methods often leave residuals such as detergents or organics with the final liposome. From a production standpoint, it is clearly preferable to utilize procedures which do not use organic solvents since these materials must be subsequently removed.

Some of the methods impose harsh or extreme conditions which can result in the denaturation of the phospholipid raw material and encapsulated drugs. These methods are not readily scalable for mass production of large volumes of liposomes.

Several methods exist for producing MLVs, LUVs and SUVs without the use of organic solvents. MLVs, free of organic solvents, are usually prepared by agitating lipids in the presence of water. The MLVs are then subjected to several cycles of freeze-thawing in order to increase the trapping efficiencies for water soluble drugs. MLVs are also used as the starting materials for LUV and SUV production.

One approach of creating LUVs, free of organic solvents, involves the high pressure extrusion of MLVs through polycarbonate filters of controlled pore size. SUVs can be produced from MLVs by sonication, French press or high pressure homogenization techniques. High pressure homogenization has certain limitations. High pressure homogenization is useful only for the formation of SUVs. In addition, high pressure homogenization may create excessively high temperatures. Extremely high pressures are associated with equipment failures. High pressure homogenization does not insure end-product sterility. High pressure homogenization is associated with poor operability because of valve plugging and poor solution recycling.

The use of liposomes for the delivery and controlled release of therapeutic drugs requires relatively large supplies of liposomes suitable for in vivo use (Ostro, M. J. and Cullis, P. R., "Use of Liposomes as Injectable Drug Delivery Systems," *American Journal of Hospital Pharmacy*, 46:1576–1587, 1989). Present laboratory scale methods lack reproducibility, in terms of quantity and quality of encapsulated drug, lipid content and integrity, and liposome size distribution and captured volume. The multidimensional characteristics of the drug and the liposome, as well as potential raw material variability, influence reproducibility.

Present liposome products are not stable. It is desirable to have final formulations which are stable for six months to two years at room temperature or at refrigeration temperature. Stability requirements have been relaxed by techniques for dehydrating liposomes. Dehydrated liposomes can be distributed to hospitals, free of drugs, and mixed with the drug immediately prior to use by a hospital pharmacist. However, compounding of the liposome containing drug by a pharmacist increases the cost of the therapy and adds further potential for compounding errors.

Present liposome products are difficult to sterilize. Sterility is currently accomplished by independently sterilizing the component parts—lipid, buffer, drug and water—by autoclave or filtration and then mixing in a sterile environment. This sterilization process is difficult, time consuming and expensive since the product must be demonstratively sterile after several processing steps.

Heat sterilization of the finished product is not possible since heating liposomes does irreparable damage to liposomes. Filtration through 0.22 micron filters may also alter the features of multilayered liposomes. Gamma ray treatment, not commonly used in the pharmaceutical industry, may disrupt liposome membranes. Picosecond laser sterilization is still experimental and has not yet been applied to the sterilization of any commercial pharmaceutical.

Liposomes have been used as a drug delivery vehicle for some hydrophobic drugs. Examples of hydrophobic drugs are taxoids, camptothecins, doxorubicin, michellamine B, vincristine, and cisplatin. The term "taxoid" is used to refer to paclitaxel, cephalomannine, baccatin III, 10-deacetyl baccatin III, deacetylpaclitaxel and deacetyl-7-epipaclitaxel and derivatives and precursors thereof. Paclitaxel is one example of a taxoid. Paclitaxel, also known as TAXOL™, (NSC 125973) is a diterpene plant product derived from the western yew *Taxus brevifolia*. The formula for paclitaxel is set forth below:

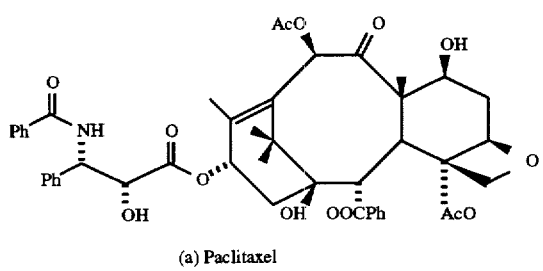

(a) Paclitaxel

This drug, currently in clinical trials, has exhibited a striking 30 to 40% response rate against advanced cases of ovarian and a number of other cancers. Currently, paclitaxel is extracted with organic solvents from the milled bark of *T. brevifolia*. This drug is in short supply.

There exists a need to maximize the therapeutic response to this drug to bring the benefits of paclitaxel therapy to as many individuals as possible. It is also necessary to minimize the adverse effect of this drug due to its natural toxicity.

Cephalomannine is another taxoid which is utilized for the treatment of cancers. Cephalomannine has the formula set forth below:

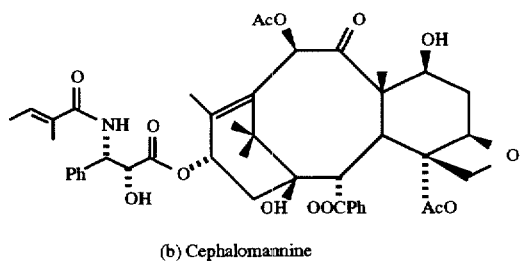

(b) Cephalomannine

Camptothecin is derived from a tree, *Camptothecin acuminata*. As used herein, the term "camptothecins" refers to camptothecin and its methoxylated analogs and carboxylated analogs and precursors which have similar biological activity and hydrophobic properties. Camptothecin is also utilized for the treatment of cancers. The formula for camptothecin is set forth below:

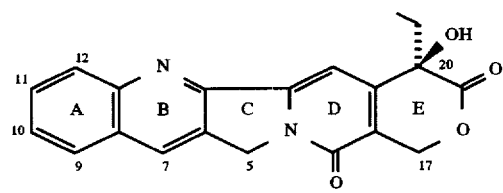

(c) Camptothecin (CPT)

Like paclitaxel, camptothecin is water insoluble and in short supply. The sodium salt of camptothecin has been utilized in initial clinical studies. Recent clinical trials suggest that several camptothecin analogs may have activity against a broad range of human/animal tumors. This composition is believed to act as an inhibitor the enzyme topoisomerase I. Due to the toxicity and hydrophobic nature of this compound, certain adverse side effects have been observed. These adverse side effects include neutropenia, nausea, vomiting, and diarrhea.

There exists a need for large scale cost effective manufacturing processes for making hydrophobic drug containing liposomes, which can meet the growing market demand. There exists a need for a process and equipment capable of continuous processing, and capable of recycling unentrapped drugs, lipids and solvents. There exists a need for a process and equipment which produces uniform liposome products.

SUMMARY OF THE INVENTION

The present invention features methods and apparatus for producing liposomes containing hydrophobic drugs. Examples of hydrophobic drugs comprise taxoids, camptothecins, doxorubicin, michellamine B, vincristine, bryostatin-1, halomon, and cisplatin. The methods and apparatus are suitable for large scale production of pharmaceutical grade liposomes which are sterile, of a predetermined size, and are substantially free of organic solvents.

The present invention features several different methods of making liposomes using critical, supercritical or near critical fluids.

One method comprises the steps of forming a solution or mixture of a phospholipid, a hydrophobic drug, an aqueous phase and a critical, supercritical or near critical fluid. The solution or mixture is decompressed to separate the critical, supercritical or near critical fluid, from the phospholipid and aqueous medium, to form one or more liposomes.

This method is referred to as the decompression method of forming liposomes in several examples. Preferably, the rate of depressurization influences the size of the liposomes formed.

As used herein, the term "phospholipid" refers to compositions which are esters of fatty acids in which the alcohol component of the molecule contains a phosphate group as an integral part. Phospholipids comprise the glycerophosphatides, containing glycerol, and the sphingomyelins containing sphingosine. Preferred phospholipids comprise phosphatidylcholine, phosphatidylethanolamine, phosphatidylserine and sphingomyelin; and synthetic phospholipids comprising dimyristoyl phosphatidylcholine, dipalmitoyl phosphatidylcholine, distearoyl phosphatidylcholine, distearoyl phosphatidylglycerol, dipalmitoyl phosphatidylglycerol, dimyristoyl phosphatidylserine, distearoyl phosphatidylserine, and dipalmitoyl serine.

In the field of physical chemistry, the term "critical fluid" refers to a substance at or above its critical temperature and at or above its critical pressure. The term "supercritical fluid" refers to a substance above its critical temperature and above its critical pressure. Supercritical fluids are sometimes designated in this application by the abbreviation "SCF." The term "near critical" is used in the sense of approaching or close to being critical. One example, without limitation, of a near critical fluid is a substance having a temperature below its critical temperature and a pressure at or above the critical pressure. Such a substance has properties which may approach those of a supercritical or critical fluid, particularly in solvating properties. These solvating properties generally approach those of a supercritical or critical fluid at a temperature between the substance's critical temperature and 75% of the substance's critical temperature and at a pressure between the substance's critical pressure and 75% of the substance's critical pressure (where pressure and temperature are defined on absolute scales).

In industrial settings where critical, supercritical and near critical fluids are used, it is common, particularly where the solvent properties are being applied, to use the term "critical" to refer to supercritical, critical and near critical fluids.

This application will use the term "SCoCoNC fluid" to represent supercritical, critical or near critical fluids. The use of the term "critical" with respect to liposomes and liposome formation refers to liposomes formed with supercritical fluid and near critical fluids as well as critical fluid. Fluids are sometimes referred to in the examples as "critical" as a convenience, even though such fluids may be supercritical, critical or near critical.

Solvating properties of SCoCoNC fluids are influenced by cosolvents and entrainers. The terms "cosolvents" and "entrainers" are used interchangeably to suggest compositions which are soluble in the SCoCoNC and impart desirable solubility features to the SCoCoNC to which they are added with respect to phospholipids and aqueous phases. Nonpolar cosolvents refer to compositions having an absence of a dipole moment or slight dipole moment, ranging approximately from 0.0 to 0.1 Debyes. Polar cosolvents refer to compositions having a dipole moment, ranging approximately from 0.1 to 1.7 Debyes.

As used herein, the term "aqueous phase" refers to a composition comprising in whole, or in part, water.

Preferably, the SCoCoNC fluid is selected from the group of compositions capable of forming critical fluids comprising carbon dioxide; nitrous oxide; halo-hydrocarbons, such as freons; alkanes such as propane and ethane; and alkenes, such as ethylene.

The "drug" is used in the sense of a therapeutic agent, a chemical or drug capable of effecting a desirable response in an individual subject. The term "hydrophobic" is used in the sense of exhibiting poor solubility in water and strong solubility in hydrocarbon solutions.

Preferably, a mixture of the aqueous phase and a solution of the phospholipid in a SCoCoNC fluid is held in a chamber of a first vessel. The solution or mixture is then decompressed as the solution passes to a second chamber or a second vessel. The second chamber allows the SCoCoNC fluid to be removed from the liposome compositions formed, at a temperature and pressure which is different from the first chamber.

Preferably the SCoCoNC fluid is recycled. To the extent that phospholipids and aqueous phase are carried over with the SCoCoNC fluid, such components may also be recycled. For convenience, liposomes formed with SCoCoNC fluid are referred to as "critical fluid liposomes" or "CFLs."

One embodiment of the present invention features an apparatus for forming liposomes containing a hydrophobic drug in accordance with the decompression method of forming liposomes. The apparatus comprises a first vessel wherein one or more phospholipids, an aqueous phase, one or more hydrophobic drugs and a SCoCoNC fluid are combined to form a mixture or solution. The hydrophobic drug is selected from the group consisting essentially of taxoids, camptothecins, doxorubicin, michellamine B, vincristine, bryostatin-1, halomon and cisplatin. The apparatus further comprises a second vessel in communication with the first vessel. The apparatus further comprises depressurization means capable of reducing the pressure of the solution or mixture. Depressurization means may be interposed between the first and second vessels or may be integral with the second vessel. The second vessel receives the solution or mixture of phospholipids, an aqueous phase and the hydrophobic drug, which form liposomes upon depressurization.

Preferably, SCoCoNC fluid is removed from the depressurization means and/or the second vessel and recycled.

One embodiment of the present invention features a method of forming liposomes, which method features an injection step. This method is referred to in several examples as the injection method of forming liposomes. This method comprises the steps of forming a solution or mixture of a hydrophobic drug, a phospholipid and a SCoCoNC. In contrast to the "decompression" method, the injection method does not involve pressurization of the aqueous phase. The hydrophobic drug is selected from the group consisting essentially of taxoids, camptothecins, doxorubicin, michellamine B, vincristine, bryostatin-1, halomon, and cisplatin. The solution or mixture is then injected through a tip or orifice into an aqueous phase to form one or more liposomes containing such drug. At the time of injection or thereafter the solution or mixture is decompressed. As a result of the decompression, the SCoCoNC fluid is separated from the phospholipids and the aqueous phase to form liposomes. The released SCoCoNC is either vented or recycled.

A preferred method uses a SCoCoNC fluid selected from the group of compositions capable of forming a critical fluid comprising carbon dioxide; nitrous oxide; halo-hydrocarbons, such as freon; alkanes such as propane and ethane; and alkenes such as ethylene.

A further embodiment of the present invention features an apparatus for forming liposomes in accordance with the injection method. The apparatus comprises a first vessel for containing a solution or mixture of a hydrophobic drug, a phospholipid and a SCoCoNC fluid. Preferably, the hydrophobic drug is selected from the group consisting of taxoids, camptothecins, doxorubicin, michellamine B, vincristine, bryostatin-1, halomon, and cisplatin. The apparatus further comprises a second vessel for containing an aqueous phase. The first vessel and the second vessel are in communication by means of injection means for injecting the mixture into the aqueous phase. Upon injection into the aqueous phase and decompression, liposomes containing a hydrophobic drug are formed.

Preferably, SCoCoNC fluid is released from the phospholipid upon injection and decompression into the aqueous phase. Preferably, the SCoCoNC fluid is recycled to the first vessel to form additional solutions or mixtures.

A further embodiment of the present invention features a method of making liposomes comprising forming a mixture of multilamellar vesicles and a SCoCoNC fluid. The multilamellar vesicles contain a hydrophobic drug. The mixture is decompressed to remove the SCoCoNC fluid to form one or more liposomes of a predetermined size. The size of the liposome can be controlled by the rate of decompression.

Preferably, multilamellar vesicles are made by hydrating a mixture of a hydrophobic drug and a phospholipid in an aqueous phase.

One embodiment of the present invention features an apparatus for forming liposomes from multilamellar vesicles. The apparatus comprises a first vessel for containing a mixture of multilamellar vesicles and a SCoCoNC fluid. The first vessel is in communication with a second vessel which second vessel is capable of decompressing the mixture to remove the SCoCoNC fluid. During decompression, one or more liposomes are formed.

One embodiment of the present invention further comprises a third vessel for forming multilamellar vesicles by hydrating phospholipids in an aqueous phase. The phospholipid contains a hydrophobic drug.

An embodiment of the present invention further features control means for determining the rate of decompression. The rate of decompression determines the size of liposomes.

Preferably, SCoCoNC fluid removed from the liposome preparation in the decompression vessel is recycled to the first vessel to form additional mixtures of multilamellar vesicles and SCoCoNC fluid.

Contact with SCoCoNC fluid may cause destruction of cellular structures particularly upon rapid decompression. Thus, embodiments of the present invention are, for the most part, self-sterilizing.

Methods and apparatus of the present invention are capable of forming liposomes which carry a hydrophobic drug. These drugs can be efficiently placed in liposomes with little loss. The liposome vehicle maximizes the therapeutic response to these drugs and minimizes toxicities related to the biological activities of the compounds and the hydrophobic physical properties. The hydrophobic drug is incorporated into ingredients which are used to form the liposome.

Liposomes made in accordance with the present invention have a narrow size distribution. That is, liposomes containing hydrophobic drugs can be made in which 80–100% of the liposomes have a size which is within 10% of the average size of the total liposome population.

A preferred size for liposomes is between 50–350 nm in diameter. Liposome preparation having a size distribution in which the average size is 100–300 nm, and more preferably 150–290 nm, may incorporate hydrophobic drugs more efficiently. Liposome preparations having a size distribution in which the average size is 150–250 nm may exhibit greater stability.

Embodiments of the present invention allow the recovery of raw materials, lipids and solvents which are not incorporated into the final liposome product. Embodiments of the present invention feature efficient drug entrapment and recovery of unencapsulated drugs. The operating parameters of the apparatus and method are consistent with other industrially applied processes. The method and apparatus are capable of operating continuously.

These and other advantages will be apparent to individuals skilled in the art in view of the drawings and detailed description which follow.

BRIEF DESCRIPTION OF THE DRAWINGS

FIG. 13 depicts a HPLC chromatogram of liposomal encapsulated camptothecin.

FIG. 15b depicting storage at room temperature (R.T.).

DETAILED DESCRIPTION OF THE DRAWINGS

The present invention will be described in detail as a method and apparatus for forming liposomes. The method and apparatus have applications for drug delivery, pharmaceuticals, cosmetics, and food processing.

Figure 1:
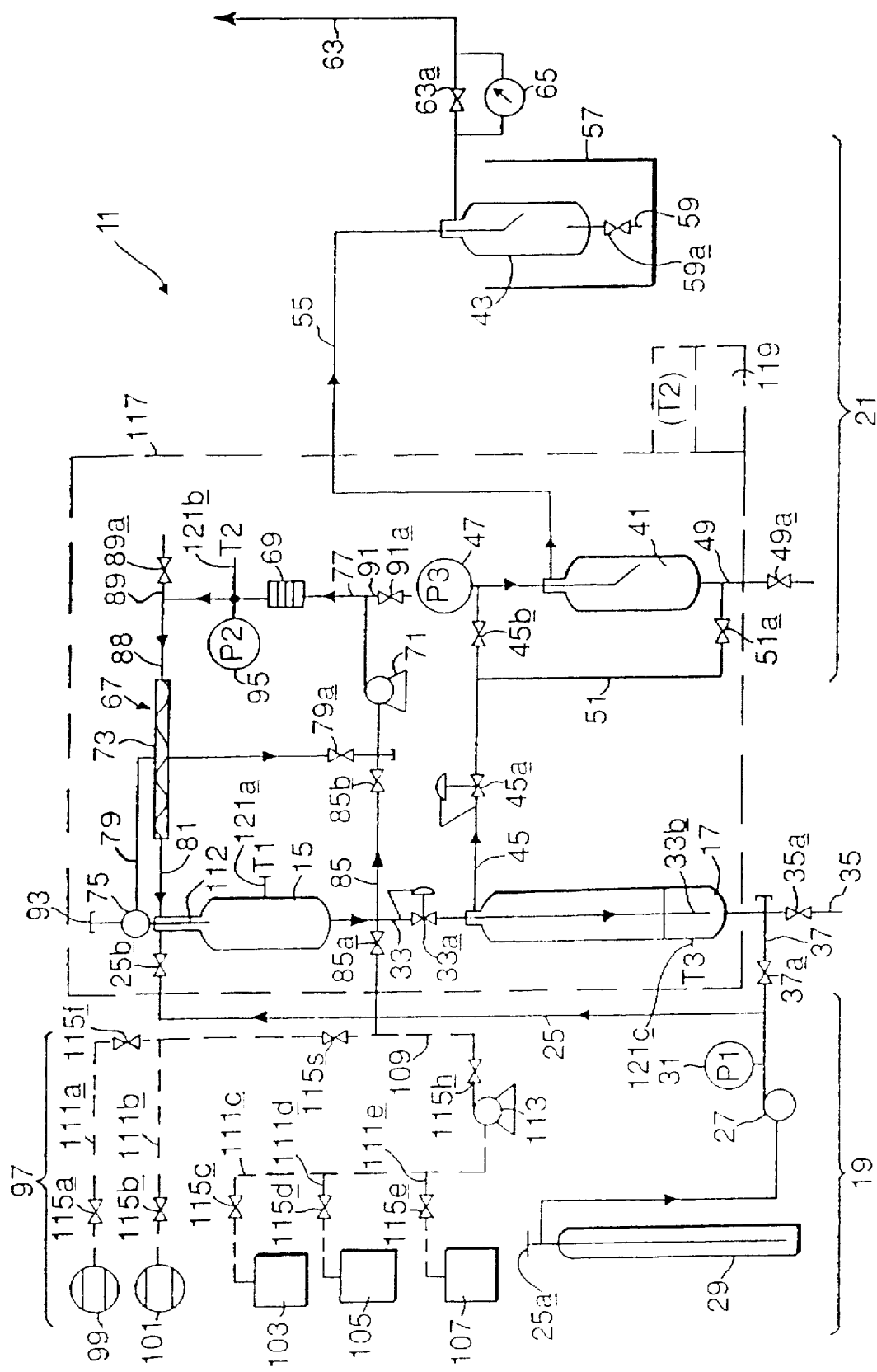
FIG. 1 schematically depicts an apparatus embodying features of the present invention.

One embodiment of the present invention is depicted in FIG. 1. An apparatus for making liposomes, generally designated by the numeral 11 is comprised of the following major elements: a first vessel 15; a second vessel 17; a source of SCoCoNC fluid, generally designated by numeral 19; and a low pressure trap assembly, generally designated by the numeral 21.

First vessel 15 is adapted to receive a supply of one or more of the following articles or compositions: phospholipids, multilamellar vesicles (MLVs), aqueous phases, SCoCoNC fluids, and therapeutic agents.

In one embodiment, first vessel 15 is capable of receiving phospholipids and an aqueous phase. First vessel 15 is in communication with the source of SCoCoNC fluid 19 to receive SCoCoNC fluid, via conduit 25. The term "communication" is used in the sense of being connected to allow fluid to be directed into or out of a vessel, conduit or the like, or to be in contact with.

Preferred SCoCoNC fluids comprise carbon dioxide, nitrous oxide, propane, ethane, ethylene, trichlorofluoromethane ($CCl_3F$), dichlorofluoromethane ($CHCl_2F$), difluorochloromethane ($CHClF_2$) and trifluoromethane ($CHF_3$). Physical properties of such gases are set forth in Table 1 below.

TABLE 1

| Fluid | Formula | BP, °C. | Pvap, psia @ 25° C. | Tc, °C. | Pc, psia | 0.75 Tc, °C. | 0.75 Pc, psia |
|---|---|---|---|---|---|---|---|
| Carbon dioxide | $CO_2$ | −78.5 | 860 | 31.1 | 1070 | −45.0 | 803 |
| Nitrous oxide | $N_2O$ | −88.5 | 700 | 36.5 | 1051 | −41.0 | 788 |
| Propane | $C_3H_8$ | −42.1 | 130 | 96.7 | 616 | 4.2 | 462 |
| Ethane | $C_2H_6$ | −88.7 | 570 | 32.3 | 709 | −44.1 | 531 |
| Ethylene | $C_2H_4$ | −103.8 | NA | 9.3 | 731 | −61.4 | 548 |
| Freon 11 | $CCl_3F$ | 23.8 | 15 | 198.1 | 639 | 80.3 | 480 |
| Freon 21 | $CHCl_2F$ | 8.9 | 24 | 178.5 | 750 | 65.6 | 562 |
| Freon 22 | $CHClF_2$ | −40.8 | 140 | 96.1 | 722 | 3.8 | 541 |
| Freon 23 | $CHF_3$ | −82.2 | 630 | 26.1 | 700 | −48.7 | 525 |

Conduit 25 is in communication with compressor 27 and storage vessel 29. Storage vessel 29 contains SCoCoNC fluid, which fluid is compelled through conduit 25 by compressor 27. Flow of SCoCoNC fluid through conduit 25 is controlled by valves 25a and 25b. Pressure in conduit 25 is monitored by pressure valve 31.

First vessel 15 receives SCoCoNC fluid from conduit 25, which SCoCoNC fluid forms a mixture with phospholipids and an aqueous phase. First vessel 15 is in communication with second vessel 17 via conduit 33.

Back pressure regulator 33a controls pressure in conduit 33. Back pressure regulator 33a reduces pressure on mixtures flowing through conduit 33, which are received by second vessel 17. In one embodiment, conduit 33 terminates in a nozzle 33b within second vessel 17.

Second vessel 17 is in communication with exit conduit 35. Valve 35a controls the flow of fluid through conduit 35.

Valve 37a controls the flow of fluid in conduit 37. Liposomes which collect in second vessel 17 are withdrawn through exit conduit 35.

Second vessel 17 is in communication with trap assembly 21. Trap assembly 21 is comprised of two major elements: first trap vessel 41 and second trap vessel 43. First trap vessel 41 is in communication with second vessel 17 via conduit 45.

Back pressure regulator 45a controls the pressure in conduit 45. Flow through conduit 45 is controlled by valve 45a. Pressure in conduit 45 is monitored by pressure meter 47.

First trap vessel 41 receives SCoCoNC fluid, and any entrained phospholipids, aqueous phase and liposomes from second vessel 17. Liposomes, phospholipids and aqueous phase are removed from first trap vessel 41 via conduit 49. Valve 49a controls movement of fluids through conduit 49.

Shunt 51 is in communication with conduit 49 and conduit 45. Shunt 51 allows sterilizing and cleaning reagents to be pumped through conduit 49 and back flushed in trap vessel 41. Valve 51a controls the flow of fluids in conduit 51.

First trap vessel 41 communicates with second trap vessel 43 via conduit 55. Second trap vessel 43 provides a second vessel to receive SCoCoNC fluid and any entrained liposomes, phospholipids and aqueous phase, as mixtures flowing from second chamber 17 and first trap vessel 41 during depressurization.

Second trap vessel 43 is maintained in ice bath vessel 57. Ice bath vessel 57 is packed with ice to control and maintain the temperature within second trap vessel 43.

Conduit 59, in communication with second trap vessel 43 allows liposomes and unincorporated phospholipids and aqueous phase to be withdrawn. Valve 59a controls the flow of fluids in conduit 59.

Second trap vessel 43 is in communication with the atmosphere by conduit 63. Flow through conduit 63 is controlled by valve 63a. Flow through conduit 63 is monitored by flow meter 65.

First vessel 15 is in communication with a phospholipid mixing assembly, generally designated by the numeral 67. Phospholipid mixing assembly 67 is comprised of the following major elements: a solids vessel 69, a circulation pump 71, a static in-line mixer 73 and three-way valve 75.

Solids vessel 69 is adapted to receive hydrophobic drugs, and phospholipids, in solid form, to be solubilized by SCoCoNC fluid. Preferably, the hydrophobic drugs are in a powdered form. Solids vessel 69 receives SCoCoNC fluid from conduit 77. Conduit 77 is in communication with circulation pump 71. Circulation pump 71 is in communication with three-way valve 75 via conduit 79. Valve 79a controls fluid movement in conduit 79.

Three-way valve 75 is in communication with static in-line mixer 73 via conduit 81. Static in-line mixer 73 is in communication with solids vessel 69 via conduit 88.

Solids vessel 69, circulation pump 71, static in-line mixer 73 and three-way valve 75, of phospholipid mixing assembly 67, define a fluid circuit. The phospholipid mixing assembly 67 is in communication with SCoCoNC fluid storage vessel 29 via conduit 25 which joins conduit 81 between three-way valve 75 and static in-line mixer 73 to allow fluid to be diverted into first chamber 15 and phospholipid mixing assembly 67.

Phospholipid mixing assembly 67 has a vent 89. Valve 89a controls the movement of fluid in vent 89.

Phospholipid mixing assembly 67 has a drain 91 in communication with conduit 77. Valve 91a controls the movement of fluid through drain 91.

Phospholipid mixing assembly 67 has an injection port 93, in communication with three-way valve 75. Injection port 93 allows materials to be injected into first vessel 15 via conduit 112, and into the phospholipid mixing assembly 67.

Phospholipid mixing assembly 67 has a pressure meter 95 in communication with conduit 88. Pressure meter 95 allows the pressure in conduit 88 to be monitored.

First vessel 15, second vessel 17, low pressure trap assembly 21 and phospholipid mixing assembly 67 are in communication with a wash assembly, generally by the numeral 97. Wash assembly 97 is comprised of the following major elements; a source of air 99, a source of water 101, a source of sodium hydroxide 103, a source of hypochlorite solution 105, and a source of methanol 107. Conduit 109 is in communication with each source via conduit branches 111a–e. Conduit 109 is in communication with conduit 25 to allow the wash reagents to enter the first vessel 15, second vessel 17, low pressure trap assembly 21, and phospholipid mixing assembly 67.

Wash reagents, such as water, sodium hydroxide solution, methanol and hypochlorite solutions, are propelled through conduit 109 by pump 113. The flow of fluids in wash assembly 97 is controlled by valves 115a, b, c, d, e, f, h and s.

The first chamber 15, second chamber 17, phospholipid mixing assembly 67, first trap vessel 41 of low pressure assembly 21, and connecting conduits are housed in box 117. Box 117 is heated by heater 119. Heater 119 is controlled by temperature sensor 121b located in conduit 88. Temperature is also sensed by temperature controllers 121a and 121c respectively located on the outside of first chamber 15, and on the outside of second chamber 17.

In operation, cleaning solvents are supplied by pump 113. Pump 113 is a close coupled gear pump rated for 6,000 ml/min against a 100 psig head. The cleaning solvents contained in vessels 101, 103, 105, and 107 included 0.1N NaOH, 10 vol. % hypochlorite solvent, and 95% methanol and deionized water. Deionized water is provided as a flush solvent at a rate of 1,200 ml/min. Instrument compressed air contained in vessel 99 (100 SCFM @100 psig) is used as a displacement and drying solvent.

The system is periodically cleaned by circulating five system volumes each of hypochlorite solution to inactivate any microorganisms present; deionized water, as a flush; caustic, to remove proteins; deionized water, as a flush; methanol, to solubilize lipids; and deionized water, as a flush. The system is blow-dried with compressed air. The apparatus is cleaned between runs by recirculating and then exhausting methanol through the apparatus 11, rinsing the second chamber 17 and low pressure trap assembly 21 with water and then drying with compressed air.

Following cleaning, the apparatus 11 is dried and brought to operating temperature. All valves are placed in a closed position. In its normal operating mode, the solids vessel 69 is first removed from the apparatus, loaded with a known quantity of phosphatidyl choline (PC)/phosphatidyl ethanolamine (PE) mixture and one or more hydrophobic drugs, and then placed back online in the phospholipid mixing assembly 69. Three way valve 75 is then turned to place injection port 93 in communication with conduit 79. Valve 79a and vent valve 89a are opened.

An optional volume of cosolvent or entrainer, such as ethanol, is then introduced via injection port 93 by means of a hypodermic syringe (not shown). Three way valve 75 is then turned to bring phospholipid mixing assembly 67 in communication with first vessel 15, and the vent valve 89a is closed. Valve 25a is then opened, supplying the SCoCoNC fluid solvent to compressor 27. Compressor 27 is turned on and immediately thereafter valve 25b is opened, introducing the SCoCoNC fluid into first vessel 15 and phospholipid mixing assembly 67. When operating pressure is attained, compressor 27 is turned off and valve 25b is closed.

After system stabilization, pump 71 is turned on and its speed adjusted. With valve 79a opened, pump 71 draws both the cosolvent from the bottom of the first vessel 15 and the SCoCoNC fluid phase from the top of the first vessel 15. The mixture is then pumped counter-clockwise, mixed by static in-line mixer 73 and directed by three way valve 75 to first vessel 15.

In most cases, an aqueous phase (either deionized distilled water or a buffered solution such as 150 mM saline phosphate buffer at pH=7.0), is introduced by a hypodermic syringe into the second vessel 17 via sample port 35 and valve 35a.

In the alternative, an aqueous phase may be introduced into first vessel 15 to form a mixture of the aqueous phase and phospholipid dissolved in a SCoCoNC fluid. As a further alternative, MLVs are introduced into first vessel 15 to form a mixture of a SCoCoNC and MLVs. Solution and mixture are introduced with sufficient lead time prior to decompression to allow the solution or mixture to achieve the same temperature as the first vessel 15 and the phospholipid mixing assembly 67.

After mixing pump 71 is turned off, valve 45b, back pressure regulator 45a, valve 63a are fully opened. Back pressure regulator 33a is slowly opened to depressurize first vessel 15 and phospholipid mixing assembly 67. Product is obtained from the second vessel 17, first trap vessel 41, second trap vessel 43 via conduits 35, 49, and 59, respectively. The volume of each collected sample is measured and recorded. Typically, 95% to 100% of the feed (aqueous and cosolvent phases) is recovered in the first trap vessel 41 and none in second trap vessel 43. The collected samples are stored at 4° C.

The liposome preparations made in accordance with the present invention have a narrow size distribution that is 80–100% of the liposomes of a preparation average size of the population. Liposome preparations can be formed in which the size is between 50–350 nm in diameter. Liposomes having a diameter of between 100–300 nm may incorporate hydrophobic drugs more efficiently than smaller liposomes. Liposomes having a diameter of 150–250 nm may exhibit greater stability than smaller liposomes.

Other features of the present method and apparatus are exemplified in the following Examples.

EXAMPLE 1

Impact of Nozzle Size and Design on the Critical Fluid Formation of Liposomes

Figure 3A:
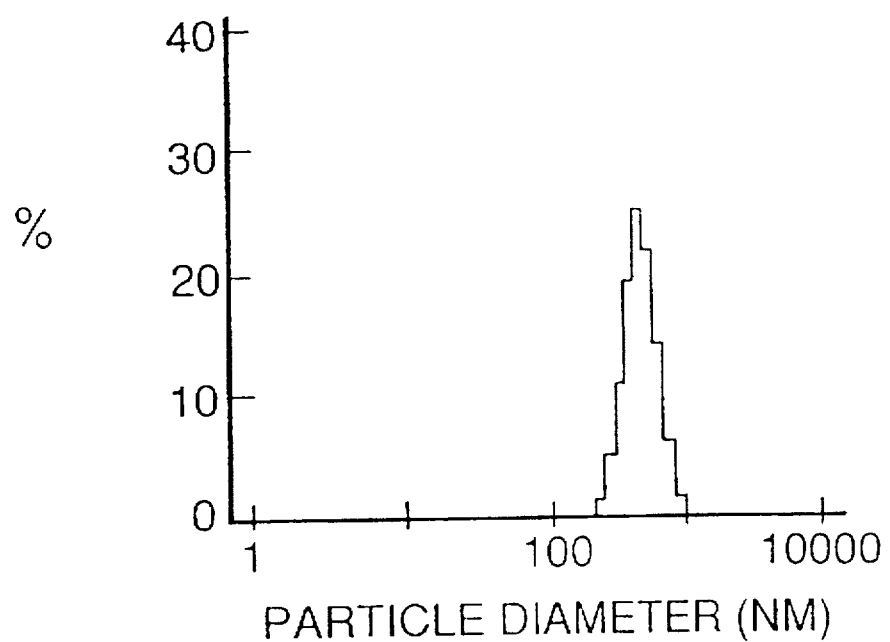
FIGS. 3(a) and (b) graphically depict a particle size analysis of liposomes formed with SCoCoNC fluid carbon dioxide with two nozzle sizes, (a) 0.5 mm and (b) of 0.06 mm.
Figure 3B:
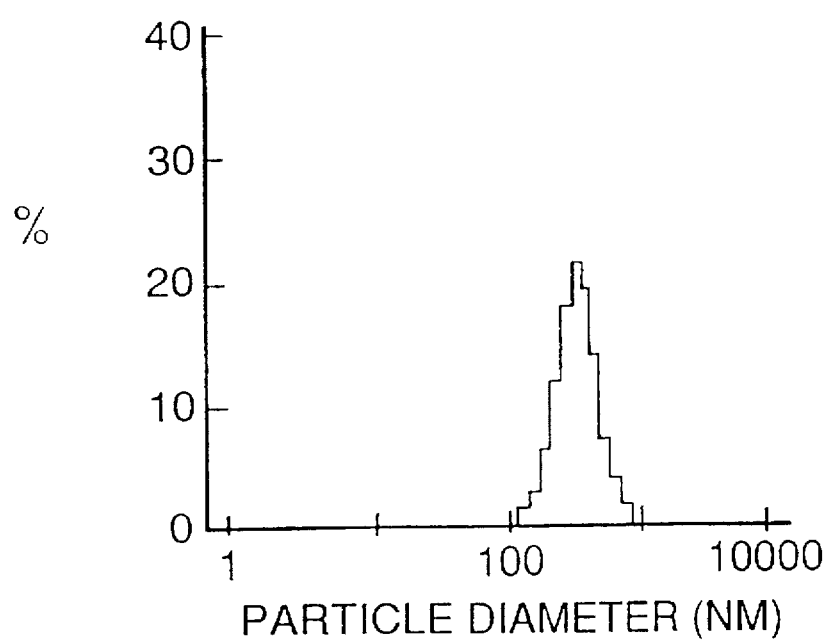

Critical fluid liposomes were formed by first solvating phospholipids in SCoCoNC fluid with/without an entrainer to form a mixture. The mixture was slowly decompressed into an aqueous phase. The number, size and characteristics of critical fluid liposomes formed are governed by a number of parameters such as the size and design of the decompression nozzle, decompressive forces, critical fluid density (temperature and pressure), interfacial forces, charge distribution, and the characteristics of the encapsulated product and the buffer solution. The impact of nozzle size on the critical fluid formation of liposomes in distilled, deionized (DDI) water is listed in Table 1, and shown in FIGS. 3(a) and (b). FIG. 3 graphically depicts particle diameter distribution of liposomes formed by SCoCoNC fluid carbon dioxide with two different nozzles. FIG. 3(a) depicts the distribution of liposomes formed with a nozzle having an inside diameter of 0.50 mm and FIG. 3(b) depicts the distribution of liposomes formed with a nozzle having an inside diameter of 0.06 mm.

TABLE 2

EFFECT OF NOZZLE SIZE ON LIPOSOME DIMENSIONS
(SCF $CO_2$ @ 4,000 psig and 60° C.)

| | | | Particle Size Analysis | | | | | |
|---|---|---|---|---|---|---|---|---|
| | | Nozzle | Sm | | Md | | Lg | |
| Exp. No. | SCF | (mm) | (nm) | % | (nm) | % | (nm) | % |
| LIP-14 | $CO_2$ | 0.50 | 0 | 0 | 478 | 100 | 0 | 0 |
| LIP-15 | $CO_2$ | 0.06 | 0 | 0 | 326 | 100 | 0 | 0 |

The liposomes formed with a nozzle diameter of 0.50 millimeters (mm) were readily visible by phase contrast microscopy. Liposomes formed with supercritical fluid carbon dioxide at 4,000 psig and 60° C., had an average size of 478 nanometers (nm). The particle size analysis was done by a size distribution processor (SDP) in a Coulter N4MD laser-based instrument. The SDP allows multimodal size analysis and reports the relative proportion of particles in each discrete size class. The single liposome population had a standard deviation (S.D.) of 180 nm and a 37% coefficient of variance (C.V.).

Liposomes formed with a 0.06 mm ID nozzle were smaller and more uniform, having an average particle size of 326 nm, (a S.D. of 150 nm and a C.V. of 44%). Based on the data in Table 2, the liposome radius appears to depend on nozzle radius to the one fifth power:

$$R'_2 = R'_1 * (r_2/r_1)^{1/5} \quad (1)$$

where R' is the radius of the liposome formed, r is the inner radius of the tip of the decompression nozzle.

Figure 2:
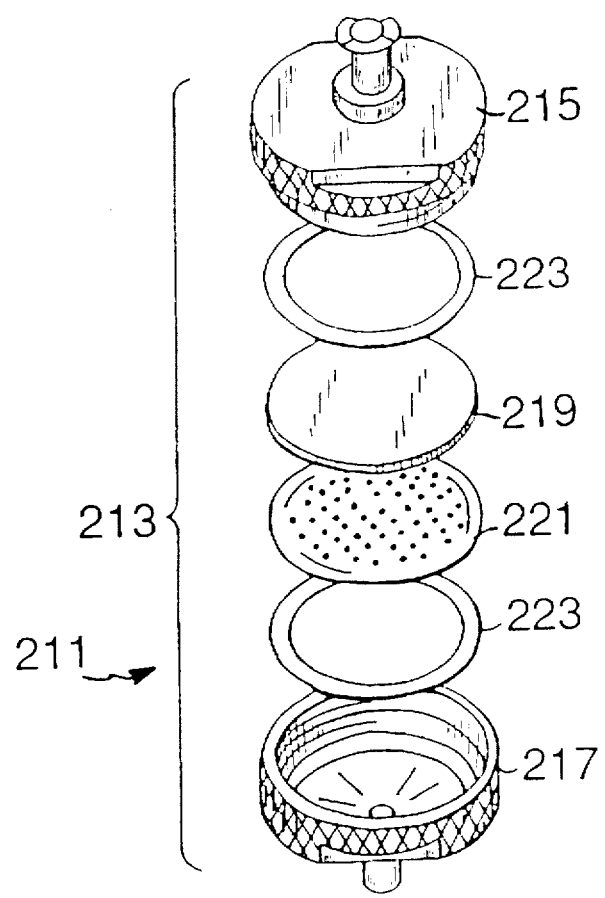
FIG. 2 is an exploded view of a nozzle assembly.

In order to further evaluate the impact of nozzle radius on the size of critical fluid liposomes (CFLs), the nozzle design was changed to incorporate a 0.22 micron (um) filter. Turning now to FIG. 2, the filter nozzle assembly, generally designated by the numeral 211 is comprised of the following major elements: a housing 213, comprising a male body 215 and a female body 217; and a filter membrane 219. The filter membrane was retained in housing 213, at the end of conduit 33 (see FIG. 1). Male body 215 and female body 217 fit together by threaded sections to form a unitary housing 213. The filter membrane 219 was an inorganic membrane with very uniform and non-tortuous pores (Alltech Associates, Inc., Deerfield, Ill.). The filter membrane 219 was supported by a 316 SS mesh screen 221 and sealed with Teflon O-rings 223.

Figure 4A:
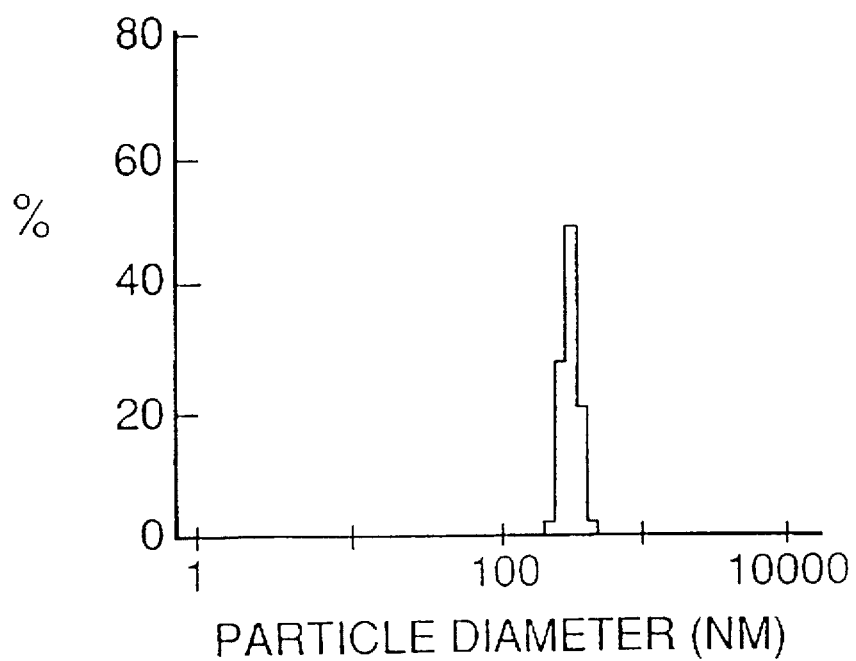
FIGS. 4(a) and (b) graphically depict a particle size analysis of liposomes formed with SCoCoNC fluid nitrous oxide and ethanol with two nozzle sizes, (a) 6.0 mm and (b) 0.22 mm.
Figure 4B:
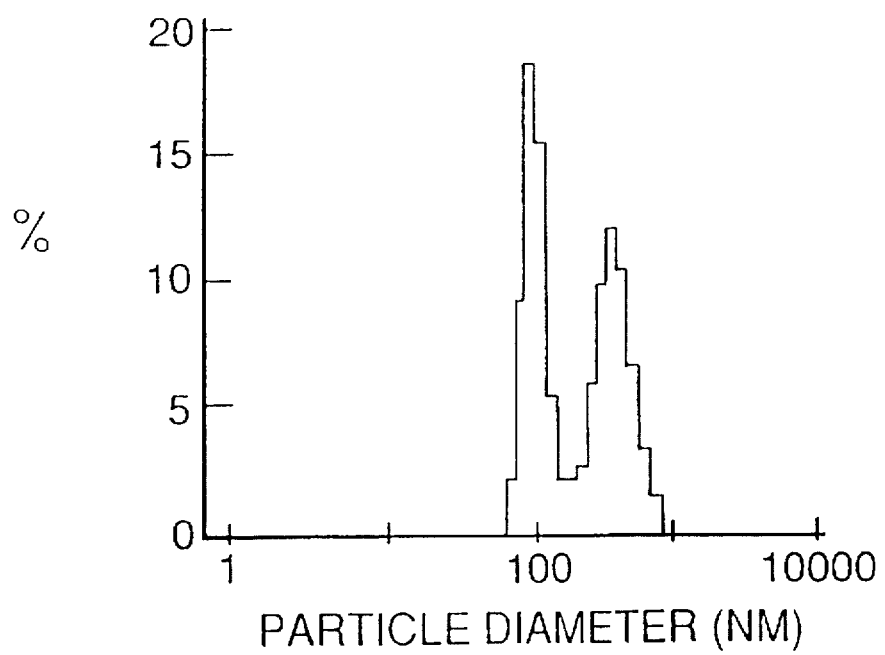

The sizes of liposomes formed by supercritical fluid $N_2O$ through the 0.06 mm needle tip and the 0.22 micron filter paper are listed in Table 2 and shown in FIG. 4. FIG. 4 graphically depicts particle size distribution of liposomes formed with SCoCoNC fluid nitrous oxide and ethanol with two different nozzle sizes. FIG. 4(a) depicts the distribution of liposomes formed with a nozzle of 0.06 mm and FIG. 4(b) depicts the distribution of liposomes formed with a nozzle of 0.22 micron.

TABLE 3

EFFECT OF NOZZLE DESIGN AND SIZE ON LIPOSOME DIMENSIONS
(SCF $N_2O$ with Ethanol @ 3,000 psig and 60° C.)

| | | | Particle Size Analysis | | | | |
|---|---|---|---|---|---|---|---|
| | | | Sm | | Md | | Lg |
| Exp. No. | SCF | Nozzle | (nm) | % | (nm) | % | (nm) | % |
| LIP-53 | $N_2O$/EtOH | 0.06 mm | 0 | 0 | 312 | 100 | 0 | 0 |
| LIP-69 | $N_2O$/EtOH | 0.22 μm | 105 | 50 | 389 | 50 | 0 | 0 |

In accordance with Equation 1, LIP-53 liposomes should have been reduced in size from 312 nm to 102 nm in LIP-69. There is at least a 50% agreement between these two experiments and Equation 1 in that the 0.22 micron filter reduced the 0.06 mm critical fluid liposomes by at least 50% to 105 nm.

A 100% size reduction may not have been possible since the 0.22 micron filter has multiple point exits which could allow neighboring bubbles to agglomerate into larger ones. The remaining experiments, unless noted, were conducted with the 0.06 mm orifice.

EXAMPLE 2

Impact of Pressure on the Formation of Liposomes

Figure 5:
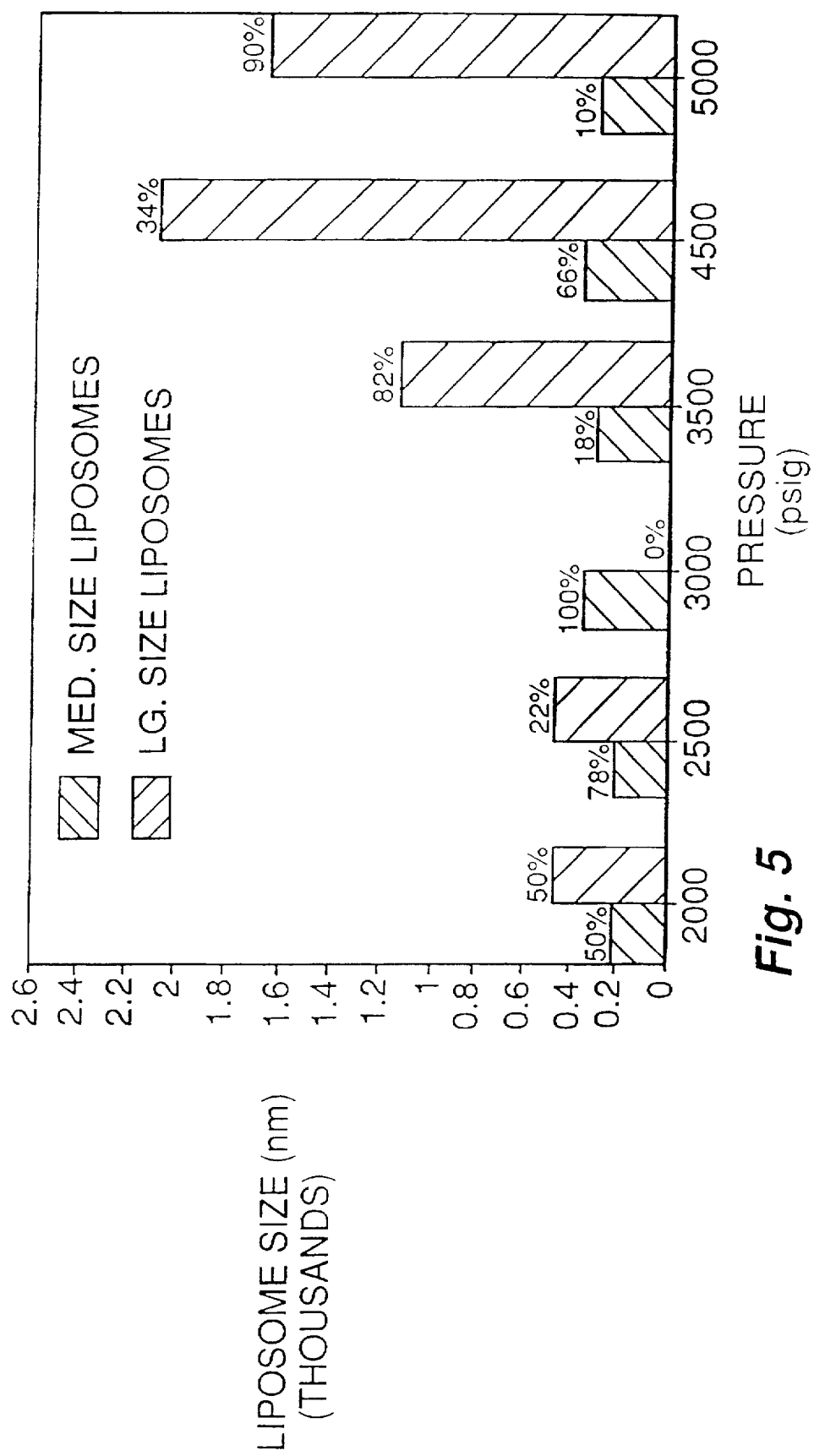
FIG. 5 is a bar graph illustrating the effect of pressure on liposome size; and, FIG. 6 is a bar graph illustrating the effect of critical fluid type on liposome size.

The effect of SCoCoNC fluid pressure on the size of liposomes formed by the injection technique is listed in Table 4 and shown as a bar chart in FIG. 5. As illustrated in FIG. 5, for each pressure, the left bar, with lines extending from bottom left to upper right, depicts medium size liposomes (100–400 mm). The right bar, with lines extending from bottom right to upper left, depicts large size liposomes (greater than 400 mm). These liposomes were all formed with a 0.06 mm decompression nozzle.

TABLE 4

EFFECT OF INITIAL CRITICAL FLUID PRESSURE ON LIPOSOME DIMENSIONS
(Critical Fluid $CO_2$ @ 60° C. and 60 mins)

| | | Particle Size Analysis | | | | | |
|---|---|---|---|---|---|---|---|
| | | Sm | | Md | | Lg | |
| Exp. No. | Pressure (psig) | (nm) | % | (nm) | % | (nm) | % |
| LIP-36 | 2,000 | 0 | 0 | 215 | 50 | 464 | 50 |
| LIP-37 | 2,500 | 0 | 0 | 215 | 78 | 464 | 22 |
| LIP-38 | 3,000 | 0 | 0 | 352 | 100 | 0 | 0 |
| LIP-48 | 3,500 | 0 | 0 | 298 | 18 | 1,150 | 82 |
| LIP-41 | 4,500 | 0 | 0 | 372 | 66 | 2,110 | 34 |
| LIP-47 | 4,500 | 0 | 0 | 317 | 37 | 1,620 | 63 |
| LIP-44 | 5,000 | 0 | 0 | 310 | 10 | 1,680 | 90 |

The increase in liposome size with initial decompression pressure is in agreement with the relationship of bubble growth formation pressure. This relationship is, however, complicated by the amount of phospholipids solubilized in the critical fluid phase and the rate of decompression. The former is significant since the most uniformly sized liposomes (100% at 352 nm) were obtained at 3,000 psig, the optimum pressure for solubilizing lecithin in supercritical fluid carbon dioxide at 60° C.

The experiments listed in Table 4 were conducted by circulating the critical fluid for 60 minutes and then slowly decompressing from the listed pressure to atmospheric conditions. The liposomes were thus formed from a variable pressure ranging from an initial pressure of 5,000 psig to 0 psig in LIP-44.

In order to evaluate the effect of a varying decompression pressure, a series of experiments were conducted in which the liposomes were formed over specific pressure intervals. The results of these experiments are listed in Table 5 below.

TABLE 5

EFFECT OF FRACTIONAL CRITICAL FLUID DEPRESSURIZATION ON LIPOSOME DIMENSIONS

| | | Particle Size Analysis | | | | | |
|---|---|---|---|---|---|---|---|
| | | Sm | | Md | | Lg | |
| Exp. No. | Pressure (psig) | (nm) | % | (nm) | % | (nm) | % |
| (Critical Fluid $N_2O$ with Ethanol @ 60° C. and 60 mins) | | | | | | | |
| LIP-64 | 3,000–2,000 | 0 | 0 | 244 | 100 | 0 | 0 |
| LIP-65 | 2,000–1,100 | 0 | 0 | 295 | 100 | 0 | 0 |
| LIP-66 | 1,100–0 | 0 | 0 | 337 | 56 | 3,140 | 44 |
| (Critical Fluid $C_2H_4$ with Ethanol @ 60° C. and 60 mins) | | | | | | | |
| LIP-104 | 3,000–2,000 | 0 | 0 | 165 | 100 | 0 | 0 |
| LIP-105 | 2,000–1,000 | 0 | 0 | 183 | 100 | 0 | 0 |
| LIP-106 | 1,000–0 | 0 | 0 | 140 | 76 | 978 | 24 |
| (Critical Fluid $C_3H_8$ with Ethanol @ 60° C. and 60 mins) | | | | | | | |
| LIP-110 | 3,000–2,000 | 0 | 0 | 120 | 62 | 1,430 | 38 |
| LIP-111 | 2,000–1,000 | 0 | 0 | 184 | 28 | 3,160 | 72 |
| LIP-112 | 1,000–0 | 0 | 0 | 136 | 24 | 3,600 | 76 |

For example in LIP-64, SCF $N_2O$ with a polar cosolvent at 3,000 psig and 60° C. was contacted with egg yolk lecithin for 60 minutes and then slowly decompressed into DDI water from 3,000 to 2,000 psig and the liposomal solution removed and replaced with fresh DDI water.

In LIP-65, liposomes were formed by slowly decompressing the remaining critical fluid mixture from 2,000 psig to 1,100 psig.

Finally, in LIP-66, the critical fluid mixture is decompressed from 1,100 psig to atmospheric conditions.

It should be noted that equal volumes of aqueous phases were used in each of the three stages of decompression. The particle size analyses indicate that a unimodal, relatively small distribution of liposomes was formed at pressures above the critical pressure of $N_2O$ which is 1,040 psig. A significant fraction of larger liposomes are formed in decompressing from 1,000 psig to atmospheric conditions. Similar fractional decompression effects on liposome size are shown in Table 5 for ethylene/ethanol and propane/ethanol mixtures.

It should be noted that the fractional nitrous oxide/ethanol decompression series was conducted with chicken egg yolk lecithin and a 0.06 mm decompression nozzle; the remaining decompression series in Table 5 were conducted with pure phosphatidyl choline in ethanol with a 0.5 mm decompression nozzle. The larger liposomes in the last stage of fractional decompression are probably formed because the density of the critical fluid changes rapidly below the critical pressure.

Operationally, decompression takes much longer at pressures around and below the critical pressure in order to retain the DDI water or aqueous buffer solution in the decompression chamber; also, the discharge volume of gas increases dramatically. This rapid increase in gas volume probably results in the formation of larger bubbles and liposomes because of Joule-Thomson cooling effects due to gas expansion. The LIP-112 sample listed in Table 5 was in fact frozen after the third stage of propane/ethanol fractional decompression.

EXAMPLE 3

IMPACT OF SCoCoNC FLUID TYPE ON THE CRITICAL FLUID FORMATION OF LIPOSOMES

Figure 6:
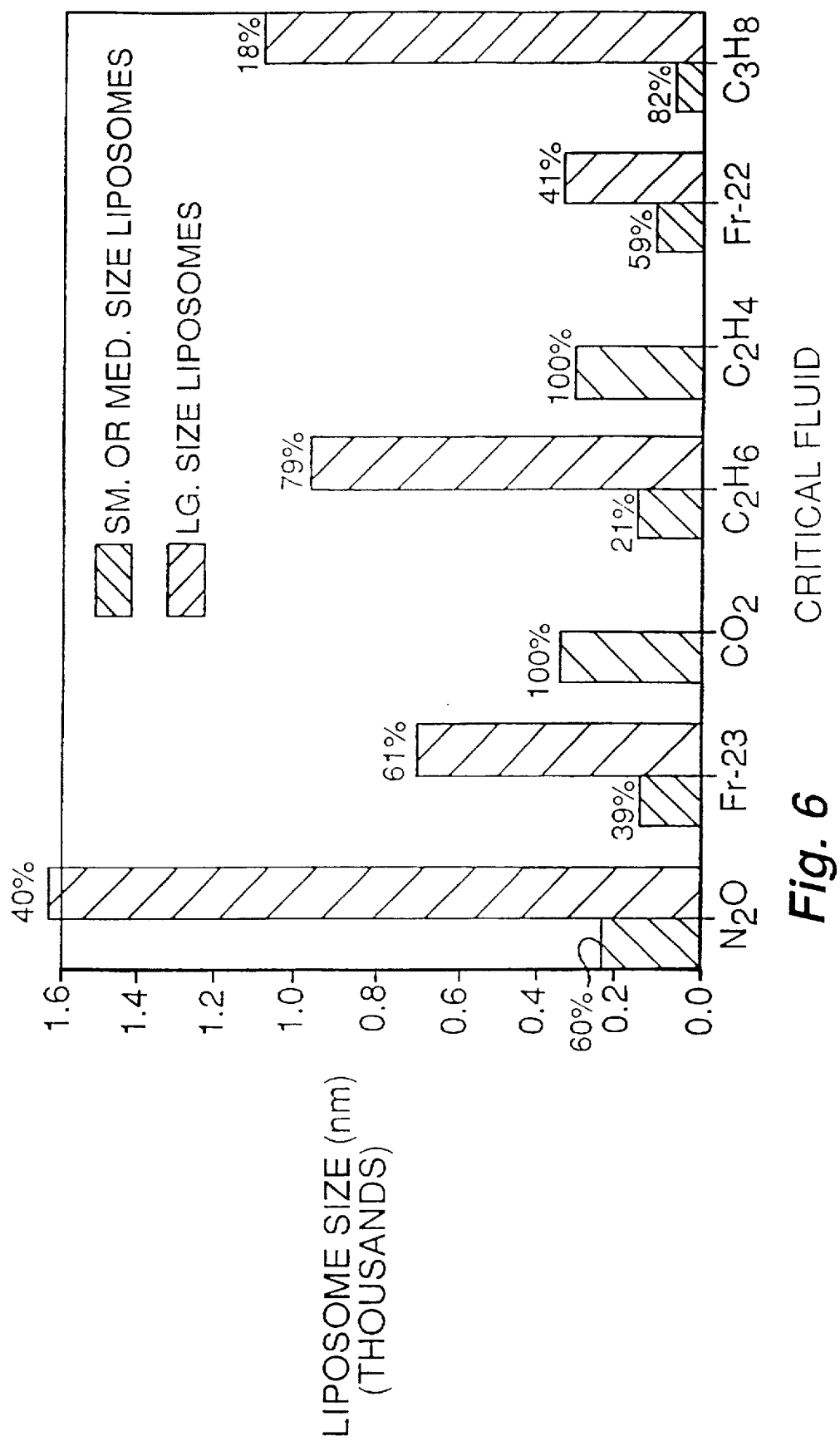

Liposomes formed by several SCoCoNC fluids are characterized in terms of particle size distributions in Table 6 and compared by bar charts in FIG. 6. As illustrated in FIG. 6, for each critical fluid, the left bar, with lines extending upward from bottom left to upper right, reflect small to medium sized liposomes. The right bar, with lines extending upward from bottom right to upper left, reflect large liposomes. These experiments were all conducted by contacting chicken egg yolk lecithin with the SCoCoNC fluid phase (without cosolvents) at 3,000 psig and 60° C. for 60 minutes, and then slowly decompressing through the 0.06 mm decompression nozzle.

TABLE 6

EFFECT OF CRITICAL FLUID TYPE ON LIPOSOME DIMENSIONS
(Critical Fluid @ 3,000 psig and 60° C. for 60 mins)

| | | Particle Size Analysis | | | | | |
|---|---|---|---|---|---|---|---|
| | | Sm | | Md | | Lg | |
| Exp. No. | SCF | (nm) | % | (um) | % | (um) | % |
| LIP-51 | $N_2O$ | 0 | 0 | 233 | 60 | 4,370 | 40 |
| LIP-61 | $CHF_3$ | 0 | 0 | 143 | 39 | 705 | 61 |
| LIP-38 | $CO_2$ | 0 | 0 | 352 | 100 | 0 | 0 |
| LIP-62 | $C_2H_6$ | 0 | 0 | 152 | 21 | 980 | 79 |
| LIP-63 | $C_2H_4$ | 0 | 0 | 320 | 100 | 0 | 0 |
| LIP-60 | $CHCIF_2$ | 106 | 59 | 348 | 41 | 0 | 0 |
| LIP-55 | $C_3H_8$ | 57 | 82 | 0 | 0 | 1,050 | 18 |
| LIP-56 | $C_3H_8$ | 57 | 82 | 0 | 0 | 1,100 | 18 |

Supercritical ethylene in LIP-63 created a unimodal albeit broad distribution (an average particle size of 320 nm and a S.D. of 300 nm) of liposomes. Decompression at subcritical pressures could have resulted in bimodal distributions for the remaining critical fluids tested.

EXAMPLE 4

Impact of Polar Entrainer or Cosolvent on the Critical Fluid Formation of Liposomes In general, polar entrainers control the size and uniformity of critical fluid liposomes as shown in Table 7 below:

TABLE 7

EFFECT OF POLAR COSOLVENTS ON NITROUS OXIDE CFLs
(SCF $N_2O$ @ 3,000 psig and 60° C. for 60 mins)

| | | Particle Size Analysis | | | | | |
|---|---|---|---|---|---|---|---|
| | | Sm | | Md | | Lg | |
| Exp. No. | Cosolvent | (nm) | % | (nm) | % | (nm) | % |
| LIP-51 | None | 0 | 0 | 233 | 60 | 4,370 | 40 |
| LIP-53 | Ethanol | 0 | 0 | 312 | 100 | 0 | 0 |
| LIP-52 | Methanol | 88 | 52 | 338 | 42 | 0 | 0 |
| LIP-54 | Acetone | 91 | 47 | 311 | 53 | 0 | 0 |

The micron sized liposome population in LIP-51, SCF $N_2O$ without a polar cosolvent, was most probably formed during decompression below nitrous oxide's critical point. The addition of 2 vol % ethanol in LIP-53 produces a narrow, unimodal distribution of liposomes having an average size of 312 nm, a standard deviation of 54 nm and a 17% coefficient of variance. Likewise, 2 vol % methanol in LIP-52 and 2 vol % acetone in LIP-54 caused the elimination of the micron sized liposome population. These two additives did, however, form distributions with average sizes around 100 nm and 300 nm. Both distributions are relatively narrow for SCF $N_2O$ with these two polar cosolvents. The added polar entrainers are most likely controlling the size of the nitrous oxide CFLs by lowering the interfacial tension between the nitrous oxide and water (5% ethanol in water reduces surface tension from 72 dynes/cm at 25° C. to 53 dynes/cm; 5% acetone in water reduces the surface tension to 56 dynes/cm). A low, more uniform interfacial tension will control the size of the bubbles and the liposomes formed. The enhanced solubility of lecithin in SCF $N_2O$ with polar entrainers could also be responsible for the reduction in the sizes and distributions of the SCoCoNC liposomes.

Polar entrainers have a similar impact on CFLs formed by near critical propane as suggested in Table 7. The addition of a 2 vol % ethanol cosolvent eliminates the micron sized liposome population formed with near critical propane, and creates a single liposome population having an average size of 196 nm and a standard deviation of 300 nm. This elimination and size reduction is probably caused by the alteration of propane-water interfacial properties, since lecithin is very soluble in near critical propane by itself. The sizes of CFLs also depend on the buffers used and the proteins to be encapsulated. Acetone has a very dramatic impact on propane CFLs, reducing the liposomes to a single population with an average size of 85 nm and a standard deviation of 83 nm. It is quite possible that methanol did not exhibit a similar impact because of the presence of salt (0.09M NaCl) in LIP-76.

TABLE 8

EFFECT OF POLAR COSOLVENTS ON SCoCoNC PROPANE LIPOSOMES
(Near Critical $C_3H_8$ @ 3,000 psig and 60° C. for 60 mins)

| | | Particle Size Analysis | | | | | |
|---|---|---|---|---|---|---|---|
| | | Sm | | Md | | Lg | |
| Exp. No. | Cosolvent | (nm) | % | (nm) | % | (nm) | % |
| LIP-56 | None | 57 | 82 | 0 | 0 | 1,100 | 18 |
| LIP-59 | Ethanol | 0 | 0 | 196 | 100 | 0 | 0 |
| LIP-76* | Methanol | 62 | 24 | 0 | 0 | 5,720 | 76 |
| LIP-77** | Acetone | 85 | 100 | 0 | 0 | 0 | 0 |

*Liposomes formed in a saline phosphate buffer with cytochrome-C.
*Liposomes formed in a phosphate buffer with cytochrome-C.

There appears to be little or no impact of polar cosolvents on liposomes formed by $CHClF_2$ (Freon-22) as shown in Table 9. It should, however, be noted that these three experiments were conducted at different pressures—LIP-60 at 3,000 psig, LIP-73 at 4,000 psig and LIP-75 at 5,000 psig. Initial pressure may have a significant influence on liposome size and distribution

TABLE 9

EFFECT OF POLAR COSOLVENTS ON $CHClF_2$ LIPOSOMES
(Near Critical $CHClF_2$ @ 60° C. for 60 mins)

| | | Particle Size Analysis | | | | | |
|---|---|---|---|---|---|---|---|
| | | Sm | | Md | | Lg | |
| Exp. No. | Cosolvent | (nm) | % | (nm) | % | (nm) | % |
| LIP-60 | None | 106 | 59 | 348 | 41 | 0 | 0 |
| LIP-73 | Ethanol | 118 | 76 | 531 | 24 | 0 | 0 |
| LIP-75 | Methanol | 84 | 66 | 473 | 34 | 0 | 0 |

EXAMPLE 5

Impact of Mode of Operation on the Formation of Liposomes

Size distributions of liposomes formed by the critical fluid injection and decompression techniques are compared and listed in Table 10.

TABLE 10

EFFECT OF OPERATIONAL MODE ON CRITICAL FLUID LIPOSOMES
($C_2H_4$/EtOH @ 3,000 psig and 60° C. for 60 mins)

| | | Particle Size Analysis | | | | | |
|---|---|---|---|---|---|---|---|
| | | Sm | | Md | | Lg | |
| Exp. No. | Mode | (nm) | % | (nm) | % | (nm) | % |
| LIP-98 | Decompression | 11 | 87 | 83 | 11 | 384 | 1 |
| LIP-99 | Injection | 0 | 0 | 63 | 90 | 1,780 | 10 |

Both experiments listed in Table 10 were conducted with a 150 mM saline phosphate buffer containing 1 mg/ml cytochrome-C and 9.1 mg/ml of chicken egg yolk lecithin. Also, a slow decompression rate of approximately 1,000 psi/min was maintained through a 0.06 mm nozzle tip for both experiments. The data in Table 10 suggests that critical fluid decompression results in a smaller particle size distribution than the critical fluid injection technique.

The effect of decompression rate on the size distribution of liposomes formed by the critical fluid decompression technique is compared in Table 11. Both experiments were conducted with identical concentrations of protein and lecithin in a saline phosphate buffer with a 0.50 mm nozzle tip. The data suggests that rapid decompression (approximately 1,000 psi/sec) does not significantly impact liposome size; in fact, slow decompression (approximately 1,000 psi/min) appears to offer good control in that a small (mean size of 92 nm), unimodal distribution was obtained in LIP-100.

TABLE 11

EFFECT OF RATE ON LIPOSOMES FORMED BY SCoCoNC DECOMPRESSION
($C_2H_4$/EtOH @ 3,000 psig and 60° C. for 60 mins)

| | | Particle Size Analysis | | | | | |
|---|---|---|---|---|---|---|---|
| | Decompression | Sm | | Md | | Lg | |
| Exp. No. | Rate | (nm) | % | (nm) | % | (nm) | % |
| LIP-9 | Rapid | 82 | 87 | 0 | 0 | 2,980 | 13 |
| LIP-100 | Slow | 92 | 100 | 0 | 0 | 0 | 0 |

EXAMPLE 6

Encapsulation Characteristics of Liposomes

Encapsulation protocols are typically "passive" in that they rely on the ability of liposomes to capture a certain aqueous volume during vesicle formation. As a result, trapping efficiencies can vary dramatically, ranging from less than 1% for small unilamellar vesicles (SUVs) to as high as 88% for some multilamellar vesicles (MLVs). Entrapment efficiencies are a function of size and nature of the method (and thus liposome manufacturing technique).

Liposomes can also be loaded by relying on their ability to sequester certain drugs in response to transmembrane ion gradients. This "active" protocol, also referred to as remote loading, involves the uptake of charged amphipathic drugs into preformed liposomes which have a transmembrane pH gradient (low intraliposomal pH when the drug involved is ionic) or a transmembrane potential gradient with exogenous ionophores such as potassium ion. For example, trapping efficiencies of 98% and drug:lipid ratios as high as 1:2.2

(w/w) can be readily achieved for doxorubicin hydrochloride in a LUV system (Mayer et al., 1985). Unlike the "passive" protocol, trapping efficiency is independent of lipid concentration. Transmembrane ion gradients not only accomplish efficient drug encapsulation but also decrease the rate of drug efflux from the vesicles as much as 30-fold.

An alternate method of obtaining high trapping efficiencies and high drug:lipid ratios is to chemically attach a hydrophobic group (e.g. a fatty acid or phospholipid) to the drug; this creates a molecule that is highly soluble in the liposome membrane. Hydrophobic drugs can be dissolved in the lipid phase prior to liposome formation. Liposomes made with SCoCoNC fluids can be loaded with a desired composition in any manner which would apply to liposomes made by conventional techniques. The loading of cytochrome-C in liposomes formed by sonication and critical fluids is summarized in Table 12. The loading was passive in the sense that cytochrome-C was present in the aqueous phase during the formation of the liposome.

achieved within five minutes, resulting in an injectable liposomal formulation (Ostro et al., 1989). Stability of liposomal formulations can also be increased by using synthetic saturated lipids or by adding antioxidants such as alpha-tocopherol and beta-hydroxytoluene to prevent phospholipid degradation.

The stability of critical fluid liposomes was examined in order to evaluate if critical fluids enhanced or decreased the stability of liposomal formulations. This examination was conducted by measuring the particle size distribution as a function of time. No special precautions, such as preparation of critical fluid liposomes under a blanket of inert gas, the use of antioxidants, or aseptic processing and collecting procedures were utilized in the preparation of critical fluid liposomes. The time stability of critical fluid liposomal formulations is listed in Table 13.

TABLE 12

SIZE AND TRAPPING EFFICIENCIES
OF CRITICAL FLUID LIPOSOMES
(Critical fluids @ 3,000 psig and 60° C. for 60 mins)

| | | | Particle Size Analysis | | | | | | |
|---|---|---|---|---|---|---|---|---|---|
| | | Lipid Conc. | Sm | | Md | | Lg | | Trapping |
| Exp. No. | SCF | (mg/ml) | (nm) | % | (nm) | % | (nm) | % | Efficiency |
| LIP-96 | Sonication | 10.0 | 11 | 85 | 97 | 15 | 0 | 0 | 13.5 |
| LIP-97 | $C_2H_4$/EtOH | 9.1 | 82 | 87 | 0 | 0 | 2,980 | 13 | 14.9 |
| LIP-98 | $C_2H_4$/EtOH | 9.1 | 11 | 87 | 83 | 11 | 384 | 1 | 12.9 |
| LIP-99 | $C_2H_4$/EtOH | 9.1 | 63 | 90 | 0 | 0 | 1,780 | 10 | 14.0 |
| LIP-85 | $C_3H_8$/EtOH | 16.6 | 0 | 0 | 166 | 54 | 998 | 46 | 27.7 |
| LIP-87 | $C_3H_8$/EtOH | 3.9 | 88 | 17 | 0 | 0 | 3,690 | 83 | 18.5 |
| LIP-89 | $N_2O$/EtOH | 3.9 | 97 | 33 | 384 | 6 | 3,000 | 61 | 33.3 |

EXAMPLE 7

Stability of Critical Fluid Liposomes

Stability of critical fluid liposomes depends on a variety of parameters such as raw material composition, purity and oxygen susceptibility, end product sterility, compatibility between encapsulated drug and liposomal materials, aqueous phase pH and ionic strength and composition, and preparation technique. Lack of stability will impact liposome size and drug retention capability. For pharmaceutical applications, liposomal formulations are desired to have a shelf-life between 6 to 24 months at 4° C.

Liposomes are subject to massive fusion and leakage during conventional freeze-drying and rehydration. By coating each side of the lipid membrane with equimolar concentrations of sugars such as glucose, free-flowing powdered liposomal preparations can be formed that retain 90% or more of the entrapped materials with no change in size of the liposomes (Crowe et al., 1985). Stability problems can also be avoided by "remote loading" preformed liposomes at the time of use (Bally et al., 1985). Remote loading can be readily accomplished by changing the pH of a preformed liposomal preparation in order to create a transmembrane pH gradient prior to adding the therapeutic drug in the required dosage. Reproducible and complete uptake of the drug is

TABLE 13

IMPACT OF NOZZLE SIZE ON TIME STABILITY OF
LIPOSOMES
(SCoCoNC $CO_2$ @ 4,000 psig and 60° C.)

| | Elapsed | | Particle Size Analysis | | | | | |
|---|---|---|---|---|---|---|---|---|
| | Time | Nozzle | Sm | | Md | | Lg | |
| Exp. No. | (days) | (mm) | (nm) | % | (nm) | % | (nm) | % |
| LIP-14 | 18 | 0.50 | 0 | 0 | 478 | 100 | 0 | 0 |
| LIP-14 | 52 | 0.50 | 0 | 0 | 509 | 100 | 0 | 0 |
| LIP-14 | 187 | 0.50 | 0 | 0 | 316 | 41 | 1,810 | 59 |
| LIP-15 | 6 | 0.06 | 0 | 0 | 326 | 100 | 0 | 0 |
| LIP-15 | 52 | 0.06 | 0 | 0 | 312 | 100 | 0 | 0 |
| LIP-15 | 187 | 0.06 | 0 | 0 | 315 | 100 | 0 | 0 |

Supercritical carbon dioxide liposomes exhibit good to excellent stability at a storage temperature of 4° C. over a six (6) month period as shown by the data in Table 13.

The smaller diameter liposomes, formed by the 0.06 mm nozzle, appear to be more stable than the larger liposomes formed by the 0.50 mm nozzle.

As a second point of comparison for critical fluid liposomes, the relative stability of liposomes formed by sonic energy can be inferred from the listing in Table 14.

TABLE 14

STABILITY OF LIPOSOMES FORMED BY SONIC ENERGY
(10 minutes @ 60° C.)

| Exp. No. | Buffer | Elapsed Time (Days) | Sm (nm) | Sm % | Md (nm) | Md % | Lg (nm) | Lg % |
|---|---|---|---|---|---|---|---|---|
| LIP-91 | DDI | 1 | 22 | 100 | 0 | 0 | 0 | 0 |
| LIP-91 | DDI | 23 | 28 | 93 | 97 | 7 | 0 | 0 |
| LIP-95 | PBS | 1 | 61 | 100 | 0 | 0 | 0 | 0 |
| LIP-95 | PBS | 24 | 40 | 90 | 216 | 10 | 0 | 0 |
| LIP-96 | PBS/Cytochrome-C | 1 | 11 | 85 | 97 | 15 | 0 | 0 |
| LIP-96 | PBS/Cytochrome-C | 24 | 0 | 0 | 109 | 79 | 956 | 21 |

The liposomes formed by sonic energy in deionized distilled (DDI) water exhibit a small amount of agglomeration after twenty three (23) days of storage at 4° C.

The time stability of liposomes formed by other critical fluids over a four (4) month period are presented in Table 15. The data indicates that the most effective critical fluids, in order of decreasing stability, were: (1) propane; (2) CHClF$_2$ (Freon-22); (3) nitrous oxide; (4) ethane; (5) CHF$_3$ (Freon-23); and (6) ethylene.

TABLE 15

EFFECT OF CRITICAL FLUID TYPE ON TIME STABILITY OF CRITICAL FLUID LIPOSOMES.
(Critical Fluid @ 3,000 psig and 60° C. for 60 mins)

| Exp.No. | SCF | Elapsed Intensity Time (days) | Sm (nm) | Sm % | Md (nm) | Md % | Lg (nm) | Lg % |
|---|---|---|---|---|---|---|---|---|
| LIP-51 | N$_2$O | 1 | 0 | 0 | 233 | 60 | 4,370 | 40 |
| LIP-51 | N$_2$O | 124 | 0 | 0 | 189 | 76 | 1,780 | 24 |
| LIP-61 | CHF$_3$ | 1 | 0 | 0 | 143 | 39 | 705 | 61 |
| LIP-61 | CHF$_3$ | 117 | 29 | 81 | 278 | 19 | 0 | 0 |
| LIP-62 | C$_2$H$_6$ | 1 | 0 | 0 | 152 | 21 | 980 | 79 |
| LIP-62 | C$_2$H$_6$ | 114 | 0 | 0 | 294 | 100 | 0 | 0 |
| LIP-63 | C$_2$H$_6$ | 1 | 0 | 0 | 320 | 100 | 0 | 0 |
| LIP-63 | C$_2$H$_6$ | 114 | 0 | 0 | 238 | 38 | 10,000 | 62 |
| LIP-60 | CHClF$_2$ | 1 | 106 | 59 | 348 | 41 | 0 | 0 |
| LIP-60 | CHClF$_2$ | 117 | 138 | 73 | 521 | 27 | 0 | 0 |
| LIP-56 | C$_3$H$_8$ | 1 | 57 | 82 | 0 | 0 | 1,100 | 18 |
| LIP-56 | C$_3$H$_8$ | 119 | 50 | 89 | 0 | 0 | 772 | 11 |

In general, polar cosolvents improved the stability of critical fluid liposomes. This improvement is exemplified in Table 16 which shows that the stability of critical nitrous oxide liposomes is much better with methanol as an additive; both ethanol and acetone additives are better than none and have a similar impact on the stability of N$_2$O critical fluid liposomes.

TABLE 16

EFFECT OF POLAR COSOLVENTS ON TIME STABILITY OF CRITICAL FLUID LIPOSOMES
(SCoCoNC N$_2$O @ 3,000 psig and 60° C. for 60 mins)

| Exp. No. | Cosolvent | Elapsed Time (days) | Sm (nm) | Sm % | Md (nm) | Md % | Lg (nm) | Lg % |
|---|---|---|---|---|---|---|---|---|
| LIP-51 | None | 1 | 0 | 0 | 233 | 66 | 4,370 | 40 |
| LIP-51 | None | 7 | 33 | 49 | 317 | 29 | 4,090 | 22 |
| LIP-51 | None | 124 | 0 | 0 | 189 | 76 | 1,780 | 24 |
| LIP-53 | Ethanol | 1 | 0 | 0 | 312 | 0 | 0 | 0 |
| LIP-53 | Ethanol | 7 | 0 | 0 | 297 | 100 | 0 | 0 |
| LIP-53 | Ethanol | 123 | 98 | 53 | 317 | 47 | 0 | 0 |
| LIP-52 | Methanol | 1 | 88 | 52 | 338 | 42 | 0 | 0 |
| LIP-52 | Methanol | 7 | 88 | 58 | 312 | 42 | 0 | 0 |
| LIP-52 | Methanol | 123 | 97 | 62 | 345 | 38 | 0 | 0 |
| LIP-54 | Acetone | 1 | 91 | 47 | 311 | 53 | 0 | 0 |
| LIP-54 | Acetone | 7 | 100 | 47 | 332 | 53 | 0 | 0 |
| LIP-54 | Acetone | 123 | 0 | 0 | 311 | 100 | 0 | 0 |

EXAMPLE 8
Paclitaxel and Camptothecin Containing CFLs
Operational Conditions The apparatus of the type depicted in FIG. 1 was operated at an average pressure of 3,000–4,000 psig, average temperature of about 50°–60° C., and a circulation time of 60 minutes.

Two gases, ethylene and propane, were used in this Example. This example features paclitaxel and camptothecin with the understanding that other hydrophobic drugs including without limitation, cephalomannine, doxorubicin, michellamine B, vincristine, hydrostatin-1, halomon and cisplatin would perform similarly.

Under the operational conditions propane was a near critical fluid. The critical temperature of propane is 96° C. At the operating conditions for this Example, propane is considered to be a near critical fluid exhibiting solvent properties approaching that of a critical fluid. The thermodynamic properties of propane and ethylene are listed in Table 17.

TABLE 17

Relevant Thermodynamic Properties of Critical Fluids

| Critical Fluid | Formula | $T_c$ (°C.) | $P_c$ (psig) | $r_c$ (g/cc) | Dipole Moment (debyes) |
|---|---|---|---|---|---|
| Ethylene | $C_2H_4$ | 9.2 | 731 | 0.217 | 0.0 |
| Propane | $C_3H_8$ | 96.6 | 616 | 0.217 | 0.084 |

Phospholipid Raw Materials

Fresh frozen chicken egg yolk (Sigma Chemical Co., St. Louis, Mo.), which consisted of 60% phosphatidyl choline (PC) and 16.5% phosphatidyl ethanolamine (PE), soy bean phosphatidylcholine (>95% purity) (Avanti Polar Lipids, Inc., Alabaster, Ala.) were used as liposomal raw materials. Pure cholesterol (>99% purity) was also used.

Paclitaxel and Camptothecin Raw Materials

Paclitaxel was obtained by extraction from raw materials. Camptothecin was obtained from the National Cancer Institute (NCI), Washington, D.C. A mixture of paclitaxel and cephalomannine was obtained from the NCI. HPLC analysis of this mixture showed that the weight percentages of paclitaxel and cephalomannine in the mixture were 20% and 30%, respectively.

Analytical Methods

Liposomes formed by critical fluids and sonication were characterized in terms of size, stability, and efficiency of encapsulation. A submicron particle analyzer (Coulter Electronics, Inc. Model N4MD) was used to measure average particle size, size frequency distribution, and standard deviation of particle size. This computer controlled, multiple-angled instrument utilizes a laser beam to sense light scattering by the particles in its path, due to the particle's Brownian motion and by photon correlation spectroscopy to provide particle size analysis.

Figure 7:
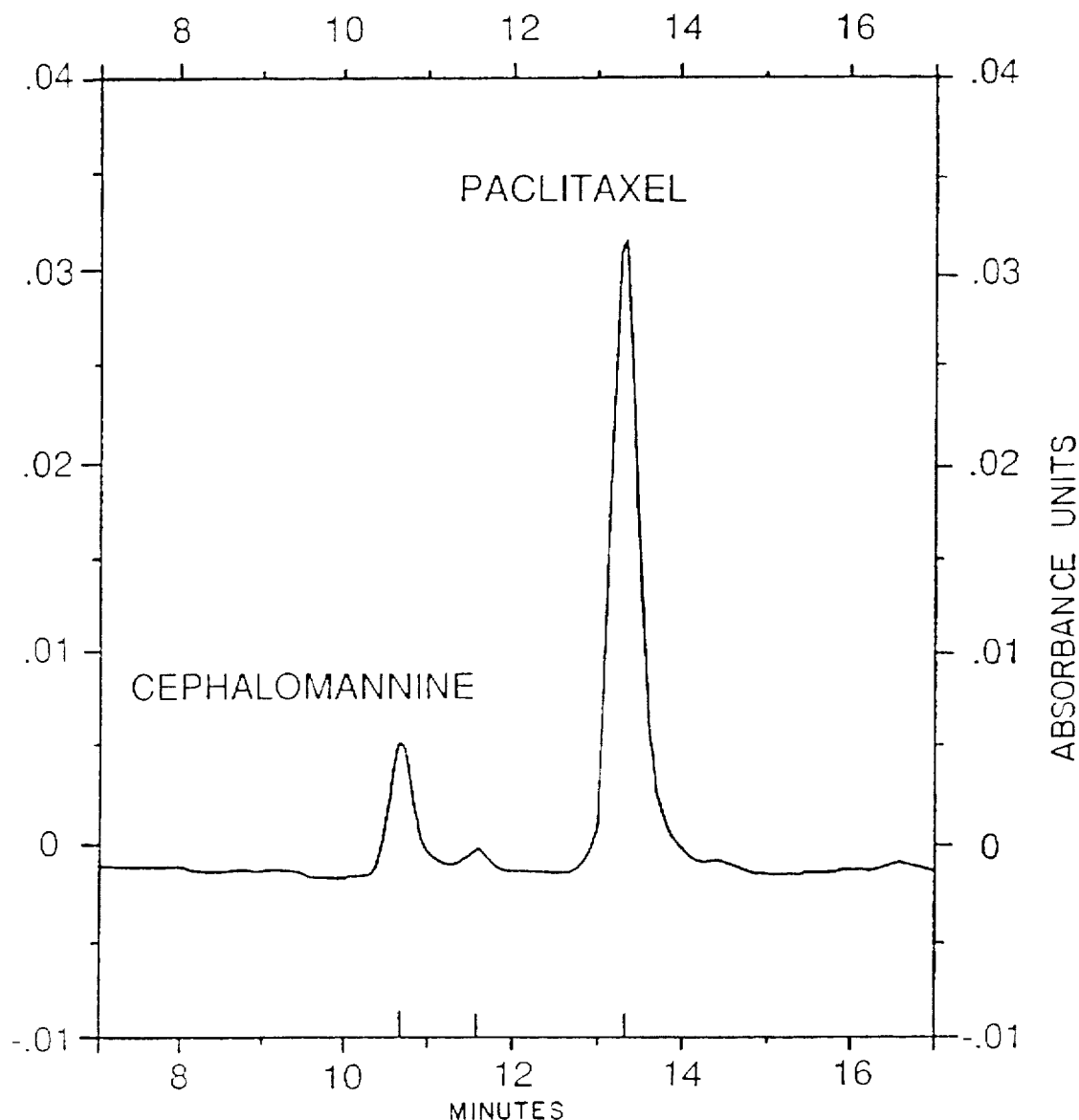
FIG. 7 depicts a HPLC chromatogram of paclitaxel and cephalomannine.

HPLC analysis for paclitaxel content in liposome formulations was performed on a 15 cm long pentafluorophenyl (PFP) column (ES Industries, Inc.) with a Waters 501 HPLC pump and a Waters 991 photodiode array detector. The flow rate and temperature were controlled at 1.5 ml/min. and 27° C., respectively. The mobile phase consisted of 44% acetonitrile, 56% water, and about 0.1% (vol.) of phosphoric acid. This system gave retention times for paclitaxel and cephalomannine around 12.5 and 9.5 minutes, respectively, with UV detection at 228 nm. The HPLC chromatogram of the paclitaxel/cephalomannine (taxoid) mixture is presented in FIG. 7.

Figure 8:
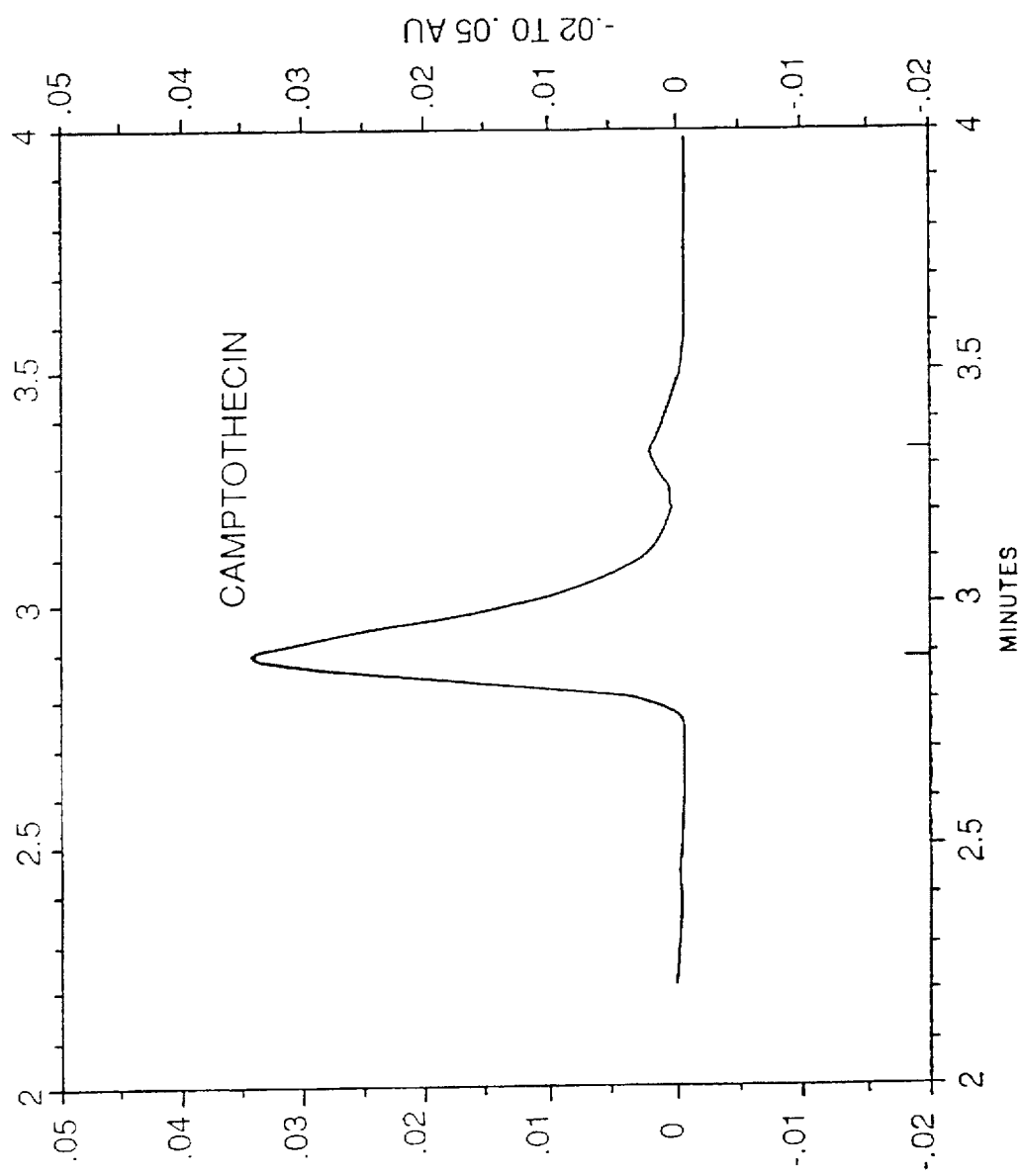
FIG. 8 depicts a HPLC chromatogram of camptothecin at a concentration of 0.04 mg/ml.

The camptothecin content of liposomes was assayed by HPLC using a reversed phase 15-cm long pentafluorophenyl (PFP) column. Using a mobile phase consisting of 80% methanol, 20% water, and 0.1% (vol.) phosphoric acid at a flow rate of 1.0 ml/min, camptothecin elutes in about 2.9 minutes. At a wavelength of 370 nm, a chromatographic scan of the camptothecin solution at a concentration of 0.04 mg/ml is shown in FIG. 8.

Gel-exclusion chromatography (GEC) was used to separate unencapsulated taxoid from liposomes, and to determine the loading efficiency of taxoid in the liposomes. A 16 mm ID×70 cm long column packed with Sephacryl S-1000 (Pharmacia LKB Biotechnology, Piscataway, N.J.) with an exclusion diameter of 260 to 300 nm was used to fractionate liposomes and separate liposomes from any unencapsulated solute. The packed GEC column was saturated with liposomal solution. This step is necessary in order to prevent subsequent liposomal formulations from sticking to the Sephacryl S1000 beads. The eluted fractions were collected by a fraction collector (ISCO, Inc. Lincoln, Nebr.). The particle size analysis and taxoid content of eluted solution were respectively analyzed by the Coulter particle analyzer, and by HPLC.

Centrifugation was applied to liposomes at 10,000 g for 15 minutes followed by filtration through a 0.22 mm filter. HPLC analysis for paclitaxel was performed before and after the filtration. This relatively simple method would give an indication of whether paclitaxel is incorporated into the liposomes.

A. Liposomes Formed by Injection

Liposomes containing paclitaxel, paclitaxel and cephalomannine, or camptothecin were formed as described in Example 1. Such liposomes were made using a 0.5 mm nozzle at a pressure of 4,000 psig and a temperature 60° C. Paclitaxel and cephalomannine, or camptothecin, in powdered form, were placed with phospholipids into a phospholipid chamber 69 of the apparatus depicted in FIG. 1. The apparatus was operated to dissolve the phospholipid and drug in SCoCoNC fluid to form a drug mixture. This mixture is injected into an aqueous phase to form liposomes.

B. Liposomes Formed by Decompression

Liposomes containing paclitaxel, or paclitaxel and cephalomannine, or camptothecin were formed as described in Example 1. That is, phospholipid, drug, aqueous phase, and a SCoCoNC fluid are thoroughly mixed in an apparatus as described in FIG. 1. The apparatus is operated at a pressure of 4,000 psig and a temperature of 60° C. This mixture is held in a first vessel and placed in fluid communication with a second vessel via a nozzle. Upon depressurization of the mixture, as the mixture moves from the first vessel to the second, or upon depressurization of the mixture upon entering the second vessel, liposomes containing drug are formed.

C. Liposomes Formed From Multilamellar Vesicles

Liposomes containing a hydrophobic drug would be made from multilamellar vesicles by first making a multilamellar vesicle in accordance with any art recognized method. A preferred method would be from a mixture of a phospholipid and the hydrophobic drug. This mixture would be hydrated in an aqueous solution to form multilamellar vesicles. The multilamellar vesicles would be mixed with a SCoCoNC fluid and decompressed to form liposomes of a uniform size.

EXAMPLE 9

Comparison of Liposome Size Distribution

Size distribution of liposomes formed by the critical fluid injection and decompression techniques, are compared in Table 18. All experimental data listed in Table 18 was obtained with average pressure and temperature around 4,000 psig and 60° C., respectively. The results in Table 18 indicate that the decompression technique resulted in a smaller particle size distribution than that of the injection technique. The difference of size distribution in liposomes formed by using two different operational modes can probably be explained by the mechanism under which liposomes are formed.

TABLE 18

Effect of Operational Mode on Size Distribution of Critical Fluid Liposomes

| | | Particle Size Analysis | | | | | |
|---|---|---|---|---|---|---|---|
| | Operation | Sm | | Md | | Lg | |
| Exp. No. | Mode | (nm) | % | (nm) | % | (nm) | % |
| LIP-54+ | Injection | 0 | 0 | 231 | 35 | 2,730 | 65 |
| LIP-169* | Injection | 0 | 0 | 157 | 38 | 954 | 62 |
| LIP-152+ | Decomp. | 97 | 89 | 547 | 11 | 0 | 0 |
| LIP-70* | Decomp. | 70.2 | 92 | 0 | 0 | 1,000 | 8 |

+Propane was used as SCoCoNC fluid.
*Ethylene was used as SCoCoNC fluid.

Without intending to limit the invention to a particular theory, in the injection technique, phospholipid solvated in the SCoCoNC fluid may deposit out at the phase boundary of critical fluid/water bubbles as result of depressurization. While these bubbles rise after detaching from the nozzle into the aqueous solution, the crystallized bilayers of phospholipids peel off, and seal themselves to form liposomes. The size distribution of liposomes will depend on several operating parameters such as: size and design of nozzle, rate of decompression, interfacial tension between the SCoCoNC fluid and aqueous medium, and pressure and temperature in the collection vessel. In this operational mode, the solvation process of phospholipids by critical fluid occurs in the high pressure circulation loop. Consequently, the liposome formation process in the decompression chamber can be operated at a different pressure and temperature environment from that required to solvate the phospholipids. This technique is well suited for the encapsulation of therapeutic proteins and compounds which are thermally labile. By its nature, the injection technique is also well suited for therapeutic proteins and compounds which are shear sensitive.

In the decompression technique, solvated phospholipids in the form of a bilayer in the critical fluid are continuously dispersed into the aqueous solution in the soaking chamber, and consequently vesiculate into liposomes. When the equilibrium stage between the critical fluid and phospholipids is reached during the circulation under constant temperature and pressure, a certain amount of solvated phospholipids will remain in the critical fluid as bilayer fragments, and circulate in the high pressure loop. During the decompression process, the mixture of critical fluid, lipid fragments and aqueous are forced through the dip tube/nozzle under large decompressive forces generated by volume expansion of the critical fluid. Existing liposomes and bilayer fragments of phospholipid may undergo collision with each other due to large shear forces, and are torn apart into smaller fragments of phospholipid. The size of these bilayer fragments depends on the pressure and the rate of decompression. These thermodynamically unstable bilayer fragments will then seal themselves rapidly to form liposomes in the decompression vessel.

In order to evaluate the effects of decompression pressure on liposome size distribution, two fractional decompression experiments were conducted. In these experiments, sample solution was collected at two different pressure intervals, the first one from operating pressure of 3500 psig down to 900 psig, which is slightly above the critical pressures of ethylene and propane, and the second one from 900 psig down to atmospheric pressure. The results of these experiments are listed in Table 19. These experiments were conducted under the same operational pressure and temperature, and with the same nozzle at the tip of the decompression tube.

TABLE 19

The Effect of Fractional Depressurization of Liposome Size Distribution
(CF: Ethylene; Circulation time: 60 min.)

| | | Particle Size Analysis | | | | | |
|---|---|---|---|---|---|---|---|
| | Decomp. Pressure | Sm | | Md | | Lg | |
| Exp. No. | Interval (psig) | (nm) | % | (nm) | % | (nm) | % |
| LIP-171 | 3,500–900 | 62 | 100 | 0 | 0 | 0 | 0 |
| | 900–0 | 0 | 0 | 118 | 69 | 992 | 31 |
| LIP-172 | 3,500–900 | 69 | 100 | 0 | 0 | 0 | 0 |
| | 900–0 | 59 | 100 | 0 | 0 | 0 | 0 |

The results from Table 19 demonstrate that it is possible to obtain liposomes with uniform size distribution by properly selecting the decompression pressure range, and the nozzle size, provided that the other conditions remain the same.

EXAMPLE 10

Characterizations of Liposome Encapsulated Paclitazel (LEP)

The liposomal samples from liposome formation processes featuring injection and decompression were centrifuged at 2,000 rpm for 30 minutes, to remove any unencapsulated solutes and large phospholipid crystals in the liposome suspension. An HPLC assay was performed to determine the paclitaxel and cephalomannine content of liposomes in the supernatant of the centrifuge tube. For comparative reasons, liposomes formed by sonication were also centrifuged and the suspended liposomes were assayed for paclitaxel and cephalomannine content. The results are presented in Table 20 below.

TABLE 20

HPLC Assay of Paclitaxel and Cephalomannine Concentration (μg/ml) From Critical Fluid Liposomes (74,000 psig and 60° C. for 60 minutes), and Sonication Liposomes (Sonicated at ~10° C. for 30 minutes)

| | Operational | Before Centrifugation | | After Centrifugation | | % Change | |
|---|---|---|---|---|---|---|---|
| Exp. No. | Mode | Paclitaxel | Cephal. | Paclitaxel | Cephal. | Paclitaxel | Cephal. |
| LIP-149 | Decomp. | 17.2 | 24.8 | 16.9 | 24.3 | (1.7) | (2.02) |
| LIP-154 | Injection | 77.6 | 90.3 | 68 | 86.5 | (12.4) | (4.2) |

TABLE 20-continued

HPLC Assay of Paclitaxel and Cephalomannine Concentration (μg/ml)
From Critical Fluid Liposomes (74,000 psig and 60° C. for 60
minutes), and Sonication Liposomes (Sonicated at −10° C. for
30 minutes)

| Exp. No. | Operational Mode | Before Centrifugation | | After Centrifugation | | % Change | |
|---|---|---|---|---|---|---|---|
| | | Paclitaxel | Cephal. | Paclitaxel | Cephal. | Paclitaxel | Cephal. |
| LIP-166 | Sonication | 85.4 | 128.3 | 46 | 73.3 | (46.3) | (42.9) |

The data clearly demonstrates that liposomes formed by injection or decompression encapsulate paclitaxel and cephalomannine. The data also suggests that injection or decompression processes capture paclitaxel more effectively than those formed by the sonication method. In LIP-166 formed by sonication, it appears that a large amount of unencapsulated paclitaxel was present in the solution, more than 45%, and that untrapped paclitaxel and cephalomannine precipitated out after centrifugation.

The incorporation of paclitaxel in liposomes was examined by utilizing Gel Exclusion Chromatography (GEC) to fractionate liposomes in different sizes, and to determine whether the paclitaxel moves with the liposomes. The eluant from the GEC column was analyzed, again, by HPLC. The particle size analysis including particle size distribution of eluted sample was also examined by the Coulter particle size analyzer.

Figure 9:
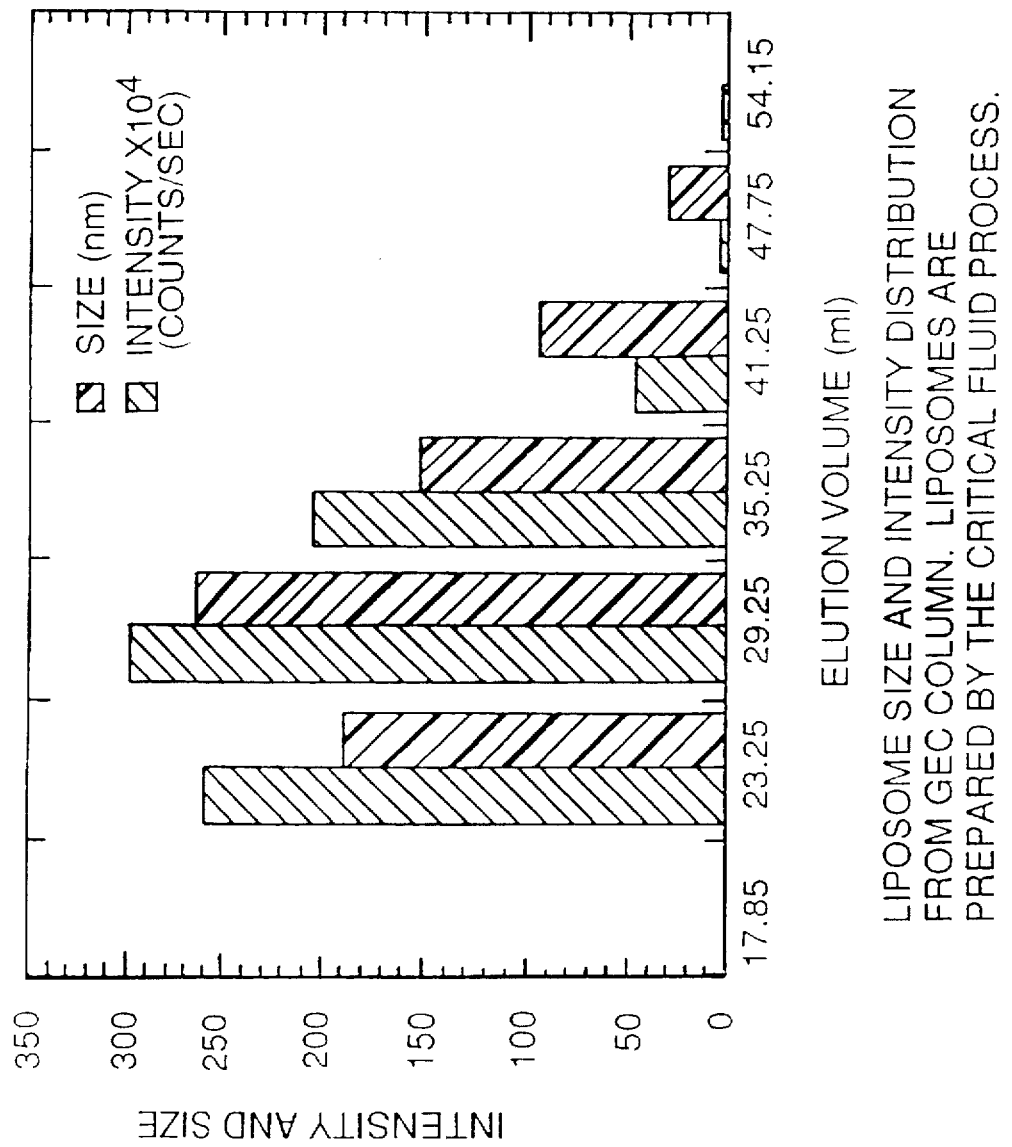
FIG. 9 depicts graphically, in bar graph form, critical fluid liposomal size distribution and intensity of liposomal solution eluted from a Gel Exclusion Chromatography (GEC) column.

GEC chromatography of the encapsulation of paclitaxel by liposomes produced by the injection process are depicted in FIG. 9. In FIG. 9, it is evident that liposomes were eluted out from the column between 18 and 40 ml. The volume fractions collected under these peaks were cloudy. The particle size intensity (counts/sec.) increases dramatically from $1.05 \times 10^4$ at about 18 ml, to $2.6 \times 10^6$ at 23 ml, and peaked around $3.0 \times 10^6$. The intensity eventually decays to $3.0 \times 10^4$ at about 54 ml. The average size of corresponding liposomes eluted from column peaked around 260 nm at 30 ml, and gradually reduced to 31 nm at about 48 ml. The first two volume fractions of LIP-154 were unimodal, and the remaining three were bimodal with a small portion of liposomes (4–20%) in the 650 to 900 nm range.

The particle size analysis for LIP-154 which had an original intensity of $2.6 \times 10^6$ or $3.0 \times 10^6$ was measured at a 1:10 or 1:20 dilution in sterile filtered water in order to obtain an intensity level within the operational range of instrument. It is quite possible that the GEC process causes liposomal agglomeration by bringing small liposomes within their charge repulsion diameters so that van der Waals forces of attraction can take effect. Our experiments also suggest that a certain amount of paclitaxel and cephalomannine incorporated in the bilayer of liposomes may be transferred to the GEC column during size fractionation.

Figure 10:
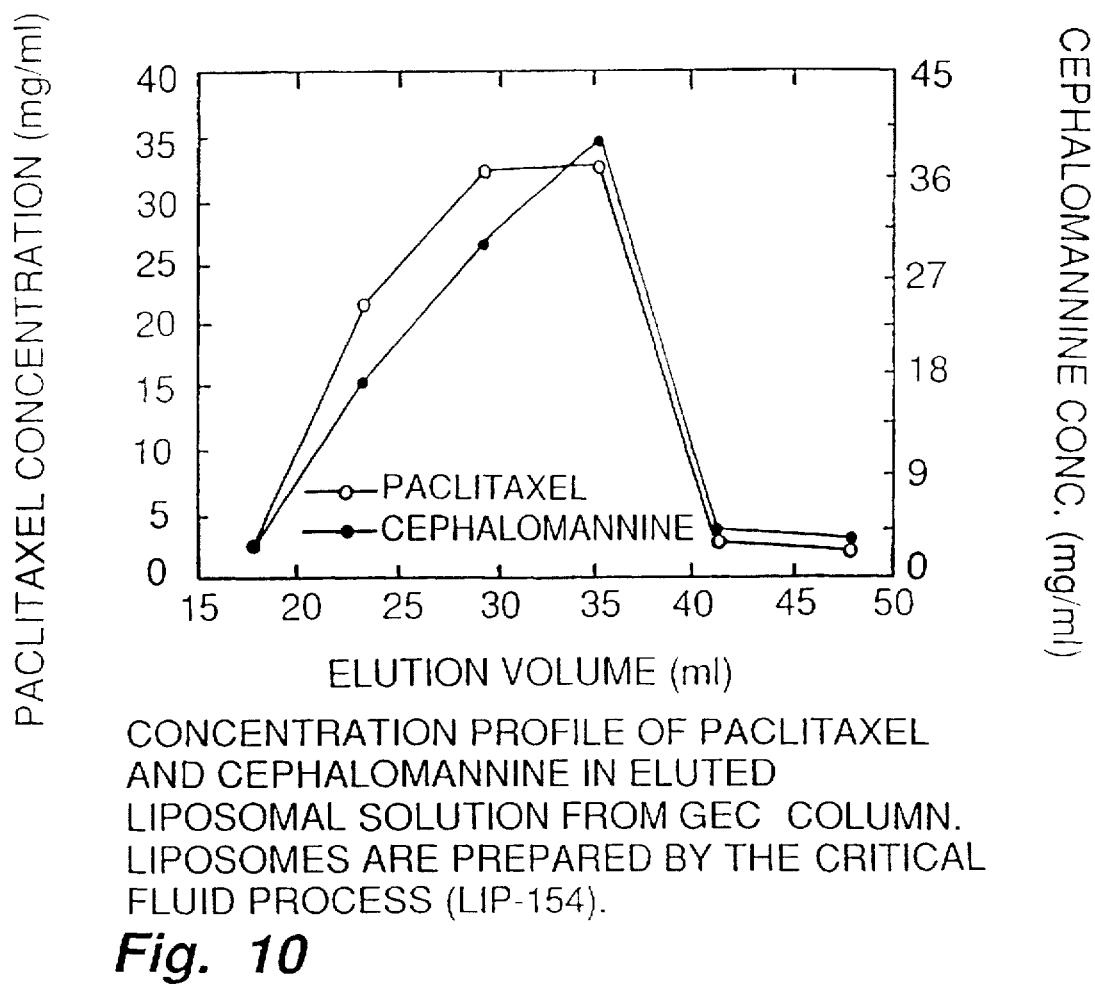
FIG. 10 depicts graphically the concentration profile of paclitaxel and cephalomannine eluted from a Gel Exclusion Chromatography (GEC) column.

HPLC analysis of paclitaxel and cephalomannine for eluted solutions of LIP-154 from the GEC column was performed. These data are represented graphically in FIG. 10, in which the concentration of paclitaxel is depicted with open circles and the concentration of cephalomannine is depicted with closed circles. Comparing FIGS. 9 and 10, it is evident that entrapped paclitaxel eluted mostly with liposomes in the 160 to 270 nm size range. The eluted peak at 18 ml has virtually identical concentrations of paclitaxel and cephalomannine, around 3 mg/ml. Both paclitaxel and cephalomannine concentrations increased sharply, and peaked around 33 mg/ml at 35 ml elution volume.

Figure 11:
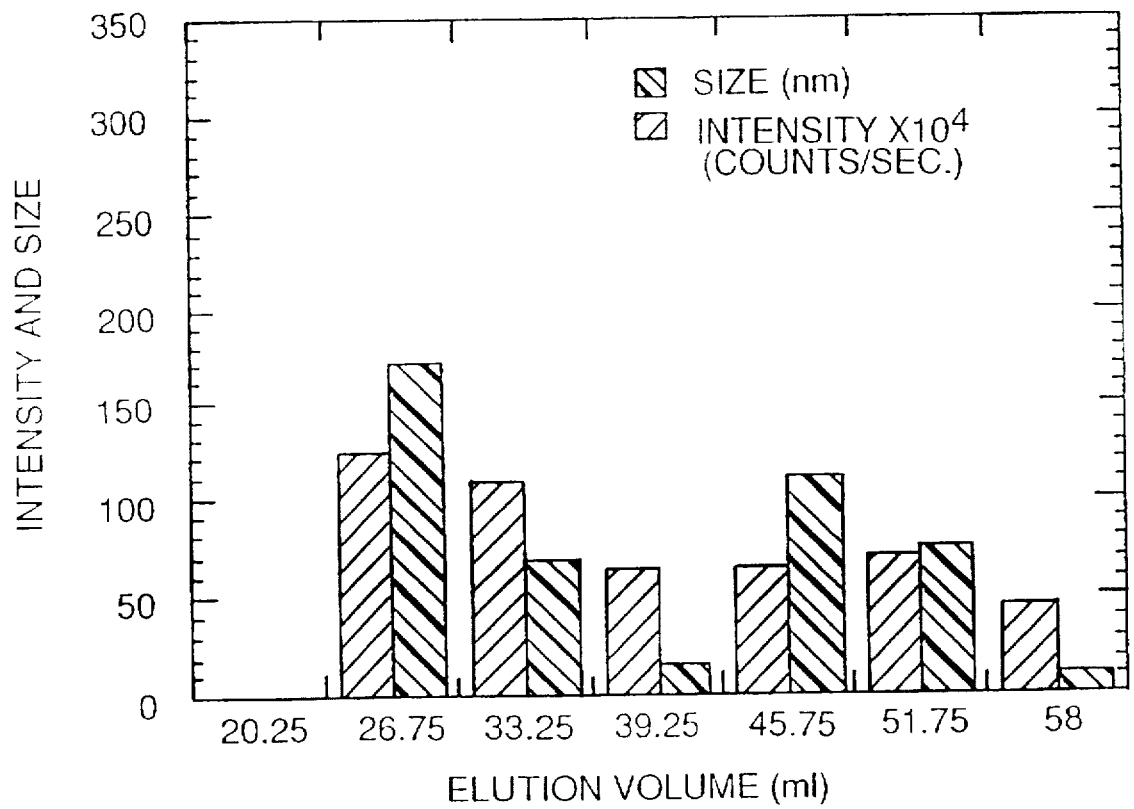
FIG. 11 depicts graphically in bar graph form, the liposome size distribution and intensity distribution of a liposomal solution eluted from GEC column, which liposomes are prepared by sonication.
Figure 12:
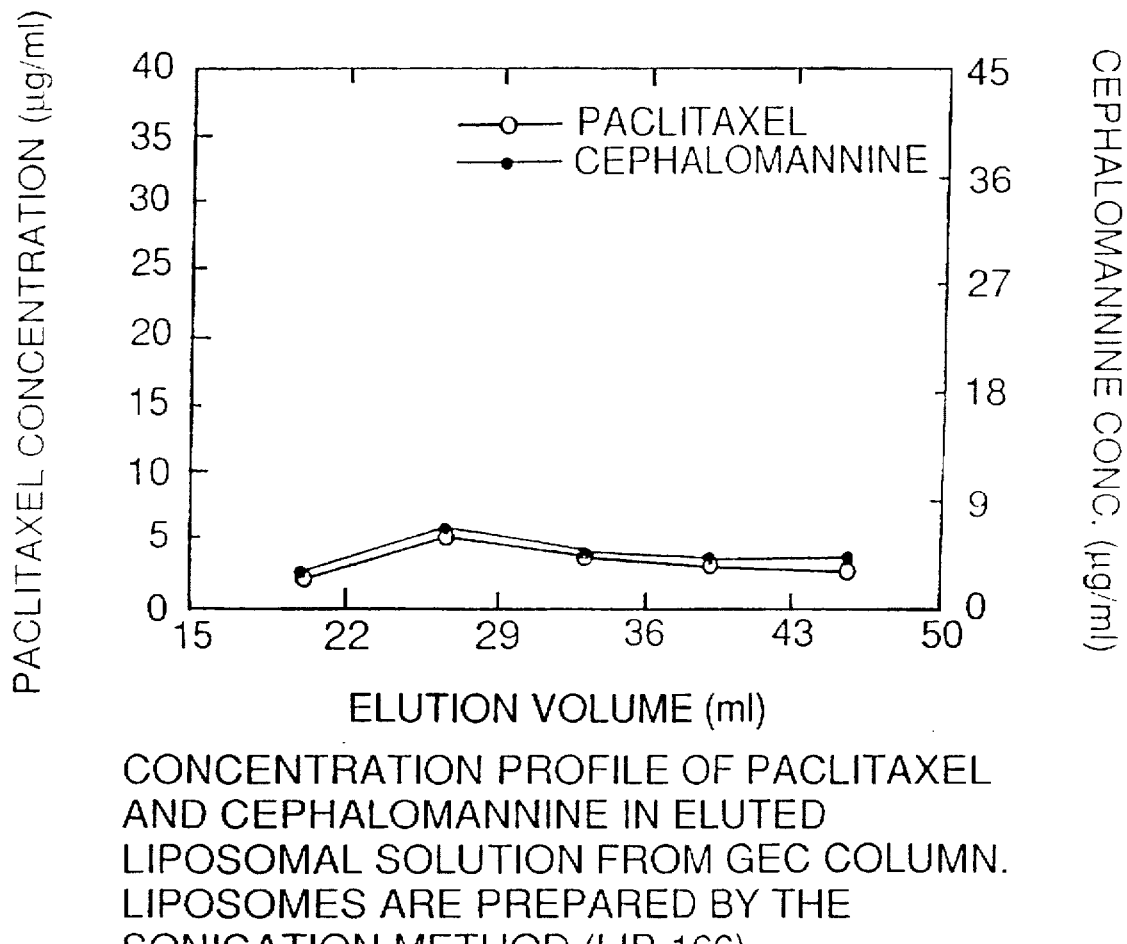
FIG. 12 depicts graphically the concentration profile of paclitaxel and cephalomannine containing liposomes from a GEC column, which liposomes are prepared by sonication.

FIGS. 11 and 12 show the analytical results of GEC fractionation of LIP-166 prepared by the sonication method (see Table 20). FIG. 11 depicts, in bar graph form, intensity and size of liposomes prepared by sonication. A large amount of liposomes eluted out of the GEC column from 20 to 40 ml, and solutions under these peaks were cloudy. Entrapped paclitaxel and cephalomannine were eluted with liposomes of around 180 nm from GEC column. These results are depicted in FIG. 12. These results are consistent with results obtained with LIP-154 which was prepared by the injection process. However, in LIP-166, the amount of paclitaxel and cephalomannine entrapped in the liposomes was much lower, about ten times, than those from the injection process. The majority of particles (86%) in LIP-166 formed by sonication are in the 38 nm range, and would not be expected to have a high paclitaxel content since small sized liposomes do not trap paclitaxel as effectively as larger liposomes.

Table 21 presents the results of two additional experiments, LIP-175 and LIP-176, in which paclitaxel was encapsulated in critical fluid liposomes. In these two experiments, cholesterol and egg yolk PC were mixed in a 1:2 ratio by weight. The fractional decompression technique was used during the depressurization process. Ethylene and propane were utilized as the critical fluid for LIP-175 and LIP-176, respectively.

TABLE 21

Concentration of Paclitaxel and Cephalomannine as well as Particle
Size Distribution in LIP-175 and LIP-176

| | | | | Particle Size Analysis | | | | | |
|---|---|---|---|---|---|---|---|---|---|
| | Decomp. Press. | Paclitaxel | Cephal. | Sm | | Md | | Lg | |
| Exp. No. | Interval (psig) | Conc. | Conc. | (nm) | % | (nm) | % | (nm) | % |
| LIP-175 | 2,800–900 | 17.9 | 31.1 | 50 | 100 | 0 | 0 | 0 | 0 |
| | 900–0 | 43.2 | 67.8 | 0 | 0 | 117 | 52 | 990 | 48 |

TABLE 21-continued

Concentration of Paclitaxel and Cephalomannine as well as Particle Size Distribution in LIP-175 and LIP-176

| | | | | Particle Size Analysis | | | | | |
|---|---|---|---|---|---|---|---|---|---|
| | Decomp. Press. | Paclitaxel | Cephal. | Sm | | Md | | Lg | |
| Exp. No. | Interval (psig) | Conc. | Conc. | (nm) | % | (nm) | % | (nm) | % |
| LIP-176 | 4,200–800 | 9.2 | 13.0 | 90 | 100 | 0 | 0 | 0 | 0 |
| | 800–0 | 16.9 | 26.6 | 0 | 0 | 166 | 69 | 1,020 | 31 |

A uniform size distribution of liposomes from the first stage of fractional decompression in both experiments was again obtained. However, paclitaxel concentration in this population of liposomes is relatively low. In our size exclusion chromatography study for LIP-154 (FIGS. 9 and 10), it was shown that paclitaxel eluted out mostly with liposomes in the 160 to 270 nm size range. This suggested that an optimal size of liposomes to encapsulate paclitaxel and cephalomannine may be in the range of 150–290 nm. In the second stage of decompression, the particles are distributed into two larger population sizes in both LIP-175 and LIP-176. This may be due to the rapid volume expansion of critical fluid below its critical pressure which is considerably larger than that in the first decompression stage. Liposomes formed in the high pressure circulation loop prior to the decompression go through a rapid disruption and fusion process, and vesiculate into larger liposomes.

EXAMPLE 11

Characterizations of Liposome Encapsulated Camptothecin (LEC)

Samples of liposomal encapsulated camptothecin, prepared by decompression in accordance with Example 1, were centrifuged at 2,000 rpm for about 30 minutes. Particle size distribution was measured on the Coulter N4MD Submicron Particle Analyzer. The HPLC analysis was conducted before and after the centrifugation as described in the section on Analytical Methods. FIG. 13 represents a typical HPLC chromatogram of liposomal encapsulated camptothecin. The same analysis was performed for liposomes containing camptothecin prepared by sonication where the same formulation of egg PC with cholesterol was dispersed in the aqueous solution. The solution was sonicated with a Branson sonifier probe (Model 450, Branson Ultrasonics Corp. Danbury, Conn.) for 30 minutes in an ice bath.

The results in the Table 22 suggest that decompression processes encapsulated camptothecin more effectively than sonication. In sonication, most camptothecin is deposited out of the aqueous solution after the centrifugation.

TABLE 22

HPLC Analysis for the Concentration of Camptothecin (μg/mil) and Particle Size Distribution From the CFL Process and Sonication

| Exp. No. | Operational Mode | Before Centrifugation Camptothecin Conc. | After Centrifugation Camptothecin Conc. | % Change |
|---|---|---|---|---|
| 1 | Decomp. | 22.5 | 23.0 | +2% |
| 2 | Sonication | 75.6 | 10.2 | −87% |

Table 23 suggests that the size of liposomes produced by decompression processes is generally larger than that prepared by the sonication method.

TABLE 23

Particle Size Analysis for Liposome Encapsulated Camptothecin Prepared by the CFL Process and by Sonication

| Exp. No. | Operational Mode | Particle Size Analysis (nm) | | | | | |
|---|---|---|---|---|---|---|---|
| | | Sm | Amt % | Md | Amt % | Lg | Amt % |
| 1 | CFL Decomp. | 122 | 64 | 0 | 0 | 4,270 | 36 |
| 2 | Sonication | 15.2 | 92 | 402 | 0.8 | 5,620 | 7 |

EXAMPLE 12

Stability Comparison of Liposome Encapsulated Paclitaxel Using Injection or Decompression Processes and Sonication The in vitro stability of liposomes will generally depend on several parameters, such as phospholipid composition and purity, oxygen susceptibility, compatibility between encapsulated drugs and liposomes, and aqueous medium conditions. Many different changes can take place in liposomes with the passage of time. The phospholipids can undergo chemical degradation such as oxidation and hydrolysis. Liposomes maintained in aqueous suspension may aggregate, fuse, or leak their contents.

Two samples (10 ml each) from experiments LIP-237 and LIP-247 were collected, and stored at 4° C. and 22° C. (room temperature), respectively. Both experiments utilized identical operational conditions (P=3,000 psi and T=50° C.), and the same phospholipid materials (soy PC and cholesterol). However, in LIP-237, a paclitaxel mixture (20% purity) was used, and in LIP-247, pure paclitaxel with >99% purity was used. The initial paclitaxel content in LIP-237 and LIP-247 was 40 and 133 ppm by HPLC, respectively. HPLC analysis was performed periodically for LIP-237 and LIP-247 at two different storage conditions. No special precautions, such as preparation of critical fluid liposomes under a blanket of inert gas, use of antioxidants, or aseptic processing and collecting procedures were used in these experiments.

Table 24 compares the stability of size distribution of LIP-237 and LIP-247 prepared by the critical fluid injection technique, with LIP-166, prepared by the conventional sonication method, (all stored at 4° C.) as a function of time. The data suggests that liposomes formed by injection processes exhibit superior physical stability to those formed by sonication. Liposomes made by sonication, LIP-166, had a large amount of small particles, 77% at 38 nm, and these liposomes appeared to fuse and aggregate together to form relatively large size particles in just 10 days. Liposomes made by the injection process (LIP-247) retained their original size even after 40 days. Liposomes formed by injection processing, LIP-237, showed signs of aggregation after 35 days; the majority of these liposomes double their size after 60 days. The relatively impure taxoid mixture used in this run may have caused this early aggregation. At room temperature storage conditions, all liposomal paclitaxel samples showed various degrees of deterioration.

TABLE 24

Comparison of Liposome Size in the Samples of LIP-237 and LIP-247, Formed by the Critical Fluid Formation Process, and of LIP-166, Formed by Sonication

| Exp. No. | Operation Mode | Elapsed Time (days) | Particle Size | | | | | |
|---|---|---|---|---|---|---|---|---|
| | | | Sm (nm) | % | Md (nm) | % | Lg (nm) | % |
| LIP-237 | Injection Technique | 1 | 152 | 100 | 0 | 0 | 0 | 0 |
| | | 60 | 0 | 0 | 355 | 100 | 0 | 0 |
| LIP-247 | Injection Technique | 1 | 218 | 100 | 0 | 0 | 0 | 0 |
| | | 40 | 213 | 100 | 0 | 0 | 0 | 0 |
| LIP-166 | Sonication Method | 1 | 38.5 | 86 | 932 | 14 | 0 | 0 |
| | | 10 | 80.8 | 69 | 846 | 31 | 0 | 0 |

Figure 14A:
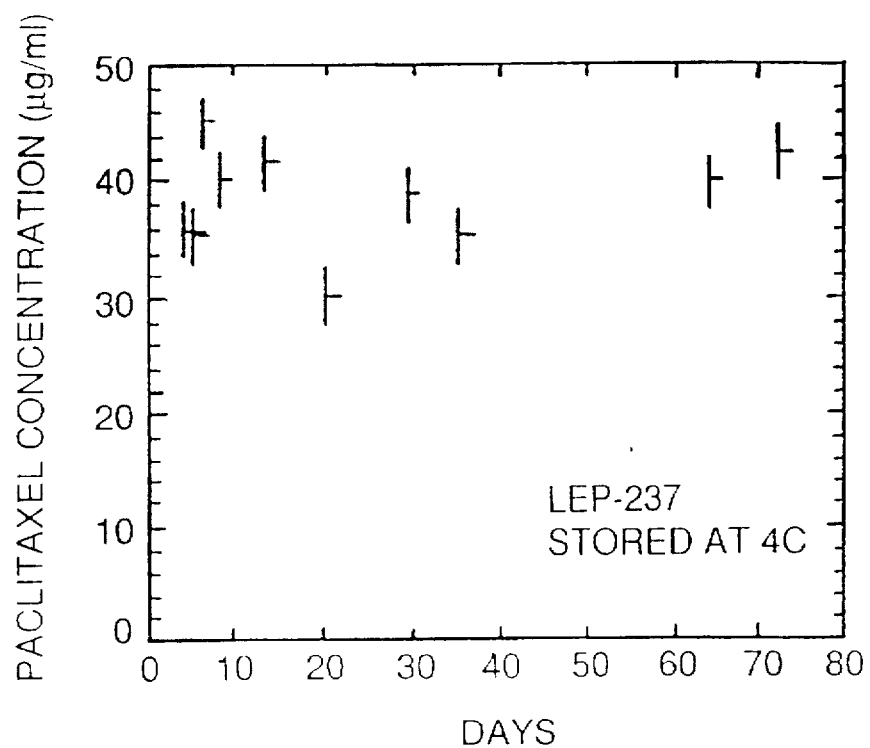
FIGS. 14a and 14b depict paclitaxel concentration as a function of time for a liposome preparation with FIG. 4a representing storage at 4° C., and FIG. 14b representing storage at room temperature (R.T.).
Figure 14B:
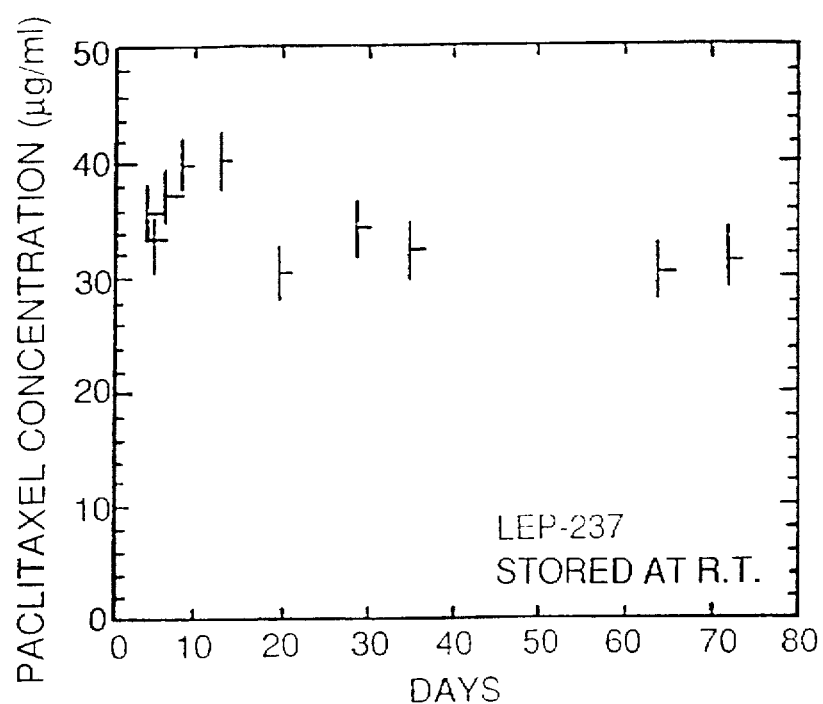
Figure 15A:
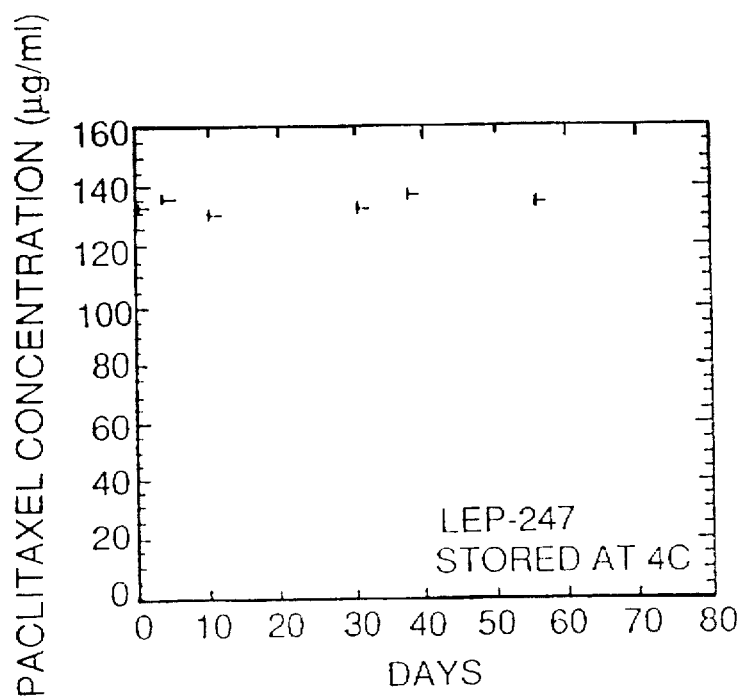
FIGS. 15a and 15b depict paclitaxel concentration profile as a function of time for a liposome preparation with FIG. 15a representing storage at 4° C.
Figure 15B:
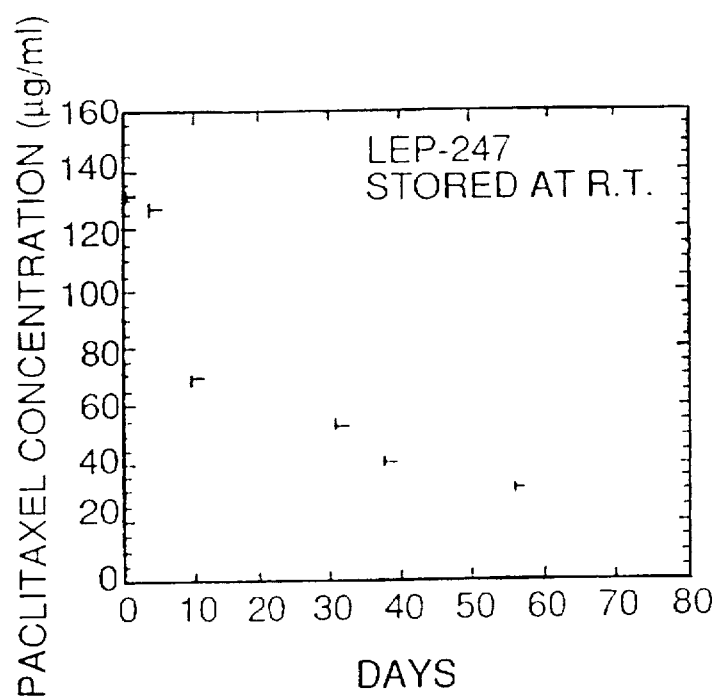

FIGS. 14 and 15 illustrate paclitaxel concentration profiles for LIP-237 and LIP-247, respectively, as a function of time and temperature. FIGS. 14a and 15a depict samples stored at 4° C., and FIGS. 14b and 15b depict samples stored at room temperature.

The results suggest that at 4° C. storage conditions, paclitaxel can remain stable in the liposome suspension for over two months. At room temperature storage condition, deterioration started after two days. These results demonstrate that the injection liposome formation process can produce physically and chemically stable aqueous-based formulations of paclitaxel. Preferably, 99such liposomes have a size distribution of 150–250 nm and, more preferably, 200–225 nm.

EXAMPLE 13

Cytotoxicity Studies of Liposome Encapsulated Paclitaxel

A. Toxicity of Liposomes Encapsulating Paclitaxel Against Colon Cancer Cell Lines An independent study on cytotoxicity of liposome encapsulated paclitaxel prepared by decompression processes was conducted. Samples of LIP-175 and LIP-176, prepared by the critical fluid decompression technique were tested against the HCT 116 human colon cancer cell line. A sample of LIP-171 which contained no paclitaxel or cephalomannine was also tested against the same cell line as a control.

In the cytotoxicity studies, a five order of magnitude dilution of the liposomal encapsulated paclitaxel was used. After seeding onto the plates for four hours, the cells were treated with liposome encapsulated paclitaxel and unencapsulated paclitaxel as a control in 0.5% DMSO buffer. The paclitaxel was left on the cells for three days after which time the plates were re-fed and thiazolyl blue was added. The reduction of the thiazolyl blue to a purple formazan product correlates in a linear way with the number of living cells in the well plates. Therefore by measuring the absorbance of this reduction product, the percent of cell survival at a given dose of paclitaxel can be quantified.

Figure 16:
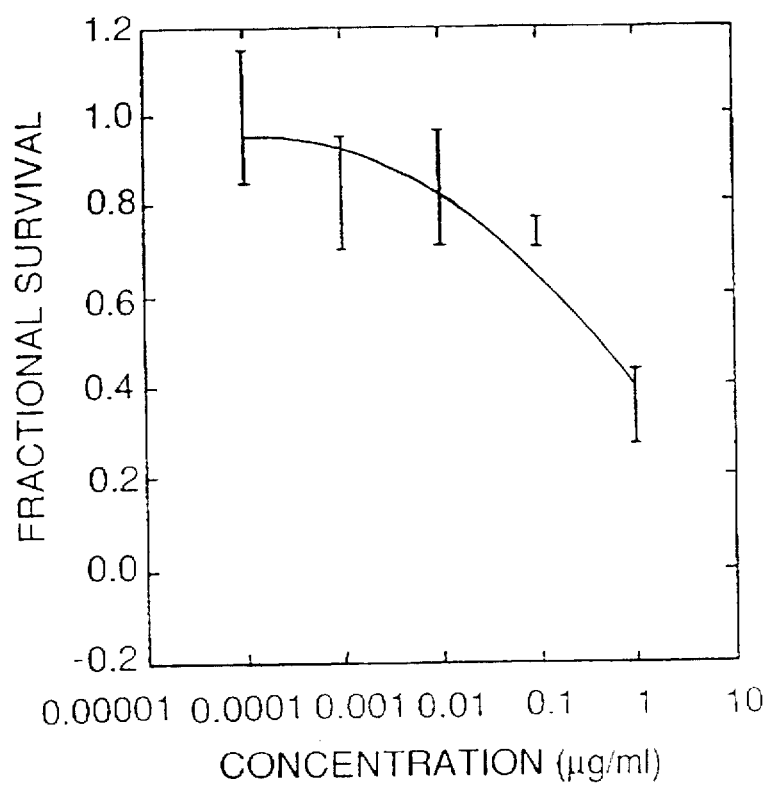
FIG. 16 depicts the toxicity profile of cells to which liposomes made in accordance with the present invention but without paclitaxel were applied as a control study.
Figure 18:
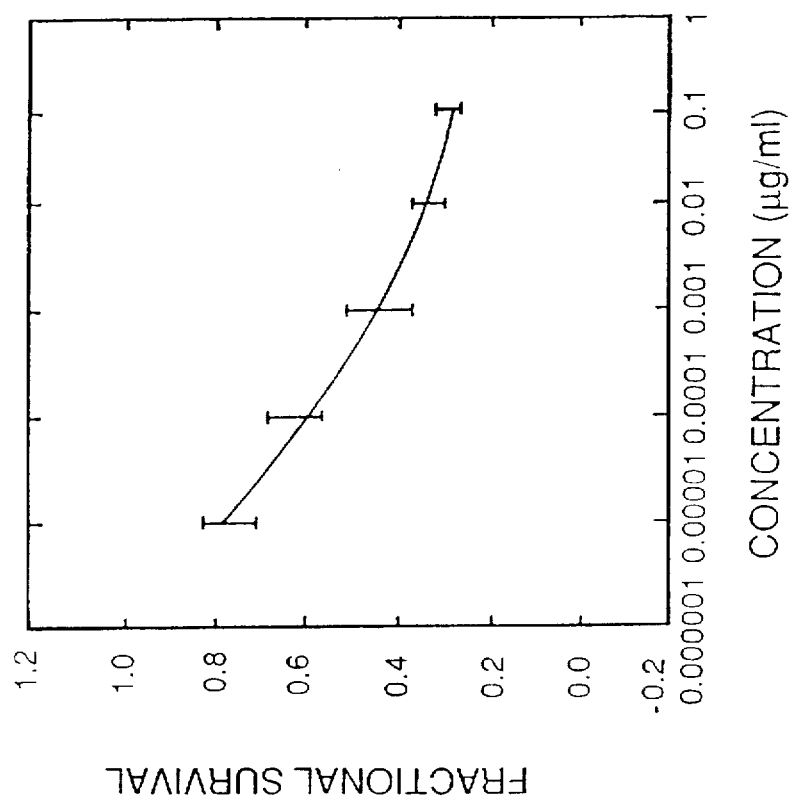
FIG. 18 depicts the toxicity profile of cells to which liposomes made in accordance with the present invention containing paclitaxel, were applied as a percent cell survival as a function of dosage level.
Figure 17:
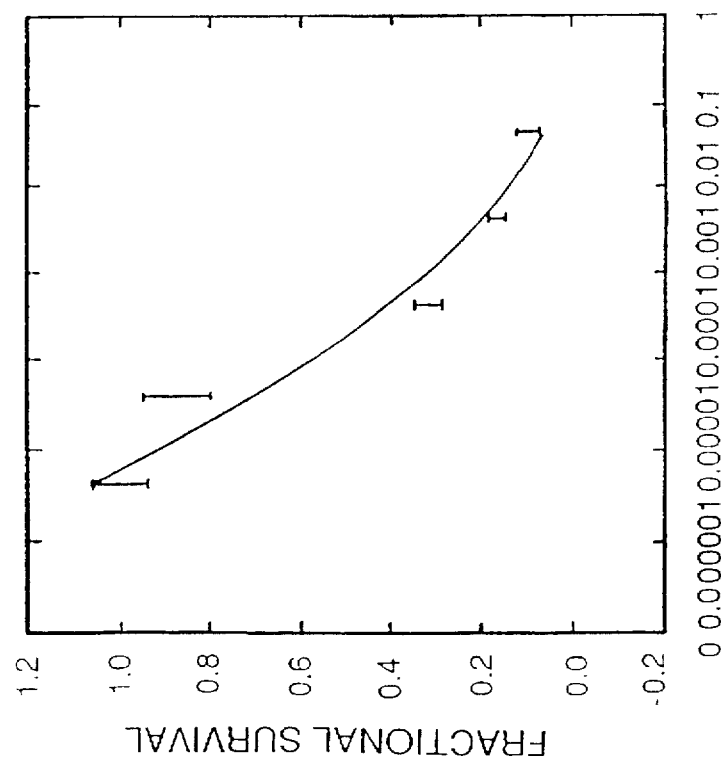
FIG. 17 depicts the toxicity profile of cells to which paclitaxel was applied, as a percent cell survival, as a function of dosage level.

The results of these studies were plotted with percent of cell survival as a function of paclitaxel concentration. Results for liposomes formed in accordance with the present methods but without paclitaxel are illustrated in FIG. 16. Results with paclitaxel, without liposomes, are illustrated in FIG. 17. Results of liposomes with paclitaxel are illustrated in FIG. 18. The data suggest that liposomes containing paclitaxel exhibit similar drug activity compared with that of paclitaxel without liposomes.

B. Toxicity Evaluation of LEP Against Breast Carcinoma Cell Lines

The ability of liposomal paclitaxel to inhibit growth of three breast carcinoma cells in tissue culture was determined. The three (3) breast cancer cell lines were MCF-3, BT-20 and MDA-MB-231.

The cell lines were grown in tissue culture flasks. A known number of cells were plated in 24-well tissue culture plates and allowed to grow overnight in a tissue culture incubator at 37° C. with 5% $CO_2$. Cells were then treated with 1.0 µg/ml concentration of liposomal paclitaxel, 1.0 µg/ml cremophor-paclitaxel, and empty liposomes (EL) diluted in cell culture media. A control group of cells were kept untreated. Cell culture media were replenished on the third day following the treatment. The treatment continued for seven (7) days.

Figure 19:
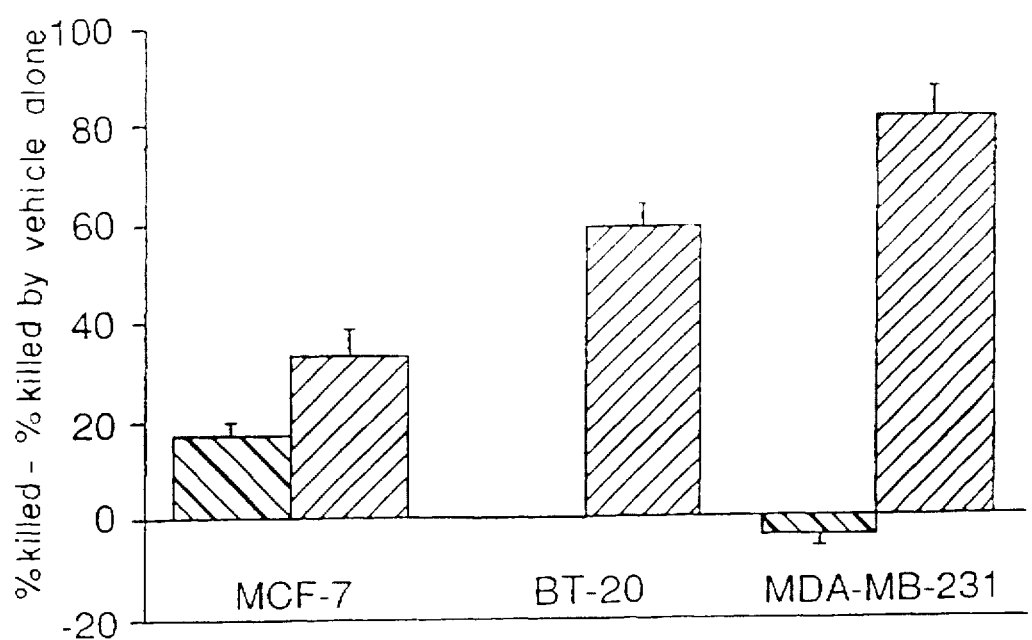
FIG. 19 depicts graphically, in bar graph form, a comparison of in vitro percent specific effect of 1.0 µg/ml liposomes containing paclitaxel made in accordance with the present invention and cremophor formulated paclitaxel (CP) for three breast cancer cell lines.

Cells in each well were counted using trypan blue. Cell viability and cell growth inhibition were calculated from the number of dead versus viable cells, and from the total number of cells grown per well. Percent specific killing for liposomal paclitaxel and cremophor-paclitaxel (CP) against breast cancer cell lines was calculated based on percentage killed from liposomal paclitaxel and cremophor-paclitaxel data and subtracting the corresponding empty liposome data. The results are illustrated in bar graph form in FIG. 19. Data representing liposomal paclitaxel is illustrated by the right hand set of bars. Data representing cremophor-paclitaxel is illustrated by the left hand set of bars. The data suggest that, at 1.0 µg/ml, liposomal paclitaxel had a much greater specific in vitro effect than cremophor-paclitaxel.

EXAMPLE 14

IN VIVO STUDIES OF LIPOSOMAL ENCAPSULATED PACLITAXEL

The objective of this study was to determine growth inhibition of breast carcinoma xenografts in nude mice by intraperitoneal (i.p.) administration of liposomal encapsulated paclitaxel. The breast cancer cell line, MDX-MB-231, was chosen based on the results of in vitro studies shown in the EXAMPLE 13. Liposomal paclitaxel from experiment LIP-247 was used in this in vivo study.

Breast carcinoma xenografts were grown in nude mice. Mice were randomly divided into four groups. Each group consisted of five mice. Tumor size was measured by a caliper and expressed in volume ($mm^3$). Treatment began when tumors reached measurable size, ~100 $mm^3$. Liposomal paclitaxels and cremophor-paclitaxel were given at a concentration of 0.295 mg paclitaxel in 0.5 ml, and an equivalent amount of empty liposomes was given for the control group via injection i.p. at two day intervals for a total of five injections. Mean Volume±Standard Error of the Mean (SEM) was recorded each time measurements were taken. All mice were sacrificed 4 weeks after the first injection.

Figure 20:
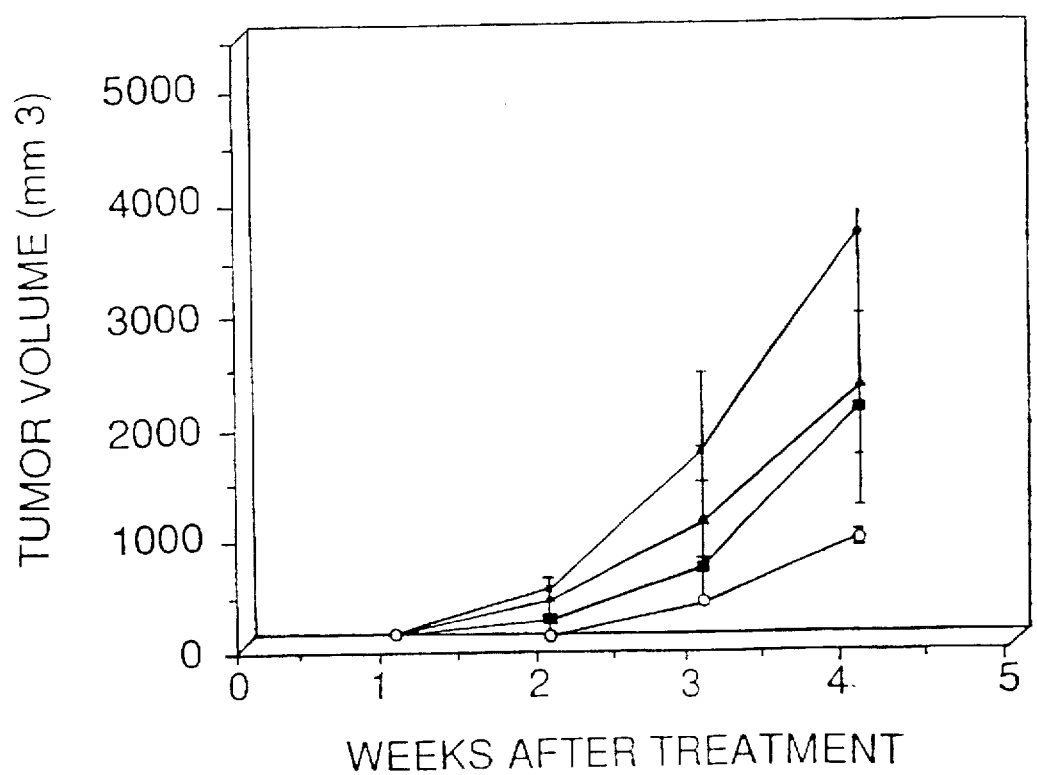
FIG. 20 depicts the antitumor activities of LEP, CP (at concentrations of 0.295 mg/ml paclitaxel), and empty liposome (EL) on breast carcinoma cell line, MDX-MB-231, xenografted into the nude mice.

The xenografts were evaluated after treatment with LEP, cremophor-paclitaxel, empty liposomes (as a control) and cremophor (as a control). The results, tumor volume versus weeks of treatment, are graphically depicted in FIG. 20. Results from mice receiving liposomal-paclitaxel are plotted with an enclosed rectangle; results from mice receiving cremophor-paclitaxel are plotted with an enclosed triangle; results from mice receiving empty liposomes are plotted with closed circles; and results from mice receiving cremophor alone are plotted with open circles. After five doses of liposomal paclitaxel, cremophor-paclitaxel and empty liposomes, liposomal-paclitaxel exhibited a better antitumor effect than the cremophor-paclitaxel.

Embodiments of the present invention allow the recovery of raw materials, lipids and solvents which are not incorporated into the final liposome product. Embodiments of the present invention feature efficient drug entrapment and recovery of unencapsulated drugs. The operating parameters of the apparatus and method are consistent with other industrially applied processes. The method and apparatus are capable of operating continuously.

Thus, while preferred embodiments of the invention have been described, the present invention is capable of variation and modification and, therefore, the present invention should not be limited to the precise details set forth, but should include such changes and alterations as fall within the purview of the following claims.

What is claimed is:

1. A method of making liposomes comprising:
   a) forming a solution or mixture of a phospholipid, one or more hydrophobic drugs and an aqueous phase in a fluid selected from the group consisting of critical, supercritical and near critical fluids; and,
   b) reducing the pressure of the solution or mixture to separate the selected fluid from the phospholipid and the aqueous phase, said phospholipid and aqueous phase forming liposomes containing said drug.

2. The method of claim 1 wherein said drug is selected from the group consisting of taxoids, camptothecins, doxorubicin, michellamine B, vincristine, bryostatin-1, halomon and cisplatin.

3. The method of claim 1 wherein said fluid is selected from the group of compositions capable of forming critical fluids consisting of carbon dioxide, nitrous oxide, halocarbons, propane, ethylene and ethane.

4. The method of claim 1 wherein said mixture or solution is decompressed as the mixture or solution exits a nozzle.

5. The method of claim 4 wherein said nozzle has one or more openings which opening has a diameter ranging from approximately 0.5 to 0.06 millimeters.

6. The method of claim 1 wherein said fluid further contains entrainers.

7. The method of claim 6 wherein said entrainers are selected from the group of compositions consisting of methanol, ethanol and acetone.

8. The method of claim 1 wherein said phospholipids are selected from the group consisting of phosphatidylcholine, phosphatidylethanolamine, phosphatidylserine, and sphingomyelin.

9. The method of claim 1 wherein said phospholipids are synthetic phospholipids selected from the group consisting of dimyristoyl phosphatidylcholine, dipalmitoyl phosphatidylcholine, distearoyl phosphatidylcholine, distearoyl phosphatidylglycerol, dipalmitoyl phosphatidylglycerol, dimyristoyl phosphatidylserine, distearoyl phosphatidylserine and dipalmitoyl phosphatidylserine.

10. The method of claim 1 wherein said phospholipids contain cholesterol.

11. The method of claim 1 wherein said liposome has a hydrophobic drug incorporated in its lipid bilayer.

12. The method of claim 2 wherein said taxoid is paclitaxel.

13. The method of claim 2 wherein said camptothecin is camptothecin.

14. A method of making liposomes comprising:
   a) forming a solution or mixture of a phospholipid, a drug and a fluid, said fluid selected from the group consisting of critical, supercritical and near critical fluid; and
   b) injecting said solution or mixture into an aqueous phase to form liposomes.

15. The method of claim 14 wherein said drug is selected from the group of hydrophobic drugs consisting of taxoids, camptothecins, doxorubicin, michellamine B, vincristine, bryostatin-1, halomon, and cisplatin.

16. The method of claim 14 further comprising the step of decompressing the solution or mixture as said solution or mixture is injected.

17. The method of claim 14 wherein said solution or mixture is injected into said aqueous phase through a nozzle.

18. The method of claim 17 wherein said nozzle has at least one opening having a diameter in the range of approximately 0.5 to 0.06 millimeters.

19. The method of claim 14 wherein said fluid is selected from the group of compositions capable of forming critical fluids consisting of carbon dioxide, nitrous oxide, halocarbons, propane, ethylene and ethane.

20. The method of claim 14 wherein said critical, supercritical or near critical fluid further comprises entrainers.

21. The method of claim 20 wherein said entrainer is selected from the group consisting of methanol, ethanol, and acetone.

22. The method of claim 14 wherein said phospholipids are selected from the group consisting of phosphatidylcholine, phosphatidylethanolamine, phosphatidylserine, and sphingomyelin.

23. The method of claim 14 wherein said phospholipids are synthetic phospholipids selected from the group consisting of dimyristoyl phosphatidylcholine, dipalmitoyl phosphatidylcholine, distearoyl phosphatidylcholine, distearoyl phosphatidylglycerol, dipalmitoyl phosphatidylglycerol, dimyristoyl phosphatidylserine, distearoyl phosphatidylserine and dipalmitoyl phosphatidylserine.

24. The method of claim 14 wherein said phospholipids contain cholesterol.

25. The method of claim 14 wherein said liposome has a hydrophobic drug incorporated in its lipid bilayer.

26. The method of claim 15 wherein said taxoid is paclitaxel or cephalomannine.

27. The method of claim 15 wherein said camptothecin is camptothecin.

28. A method of making liposomes comprising:
   a) forming a mixture of multiple bilayer liposomes and a fluid selected from the group consisting of critical, supercritical and near critical fluids, said multiple bilayer liposomes containing a hydrophobic drug; and
   b) reducing the pressure of the mixture to separate the fluid to form liposomes of a uniform size containing said drug.

29. The method of claim 28 wherein said drug is selected from the group consisting of taxoids, camptothecins, doxorubicin, michellamine B, vincristine, bryostatin-1, halomon, and cisplatin.

30. A method of making liposomes comprising:

a) forming a solution or mixture of a phospholipid, one or more hydrophobic drugs and a near critical fluid, wherein said near critical fluid is at a temperature between the critical temperature and 75% of the critical temperature of the composition of such fluid and at a pressure which is at least 75% of the critical pressure of the composition of such fluid, said fluid selected from the group of carbon dioxide, nitrous oxide, halocarbons, propane, ethylene and ethane; and, b) injecting said solution or mixture into an aqueous phase to form liposomes.

31. A method of making liposomes comprising:

a) forming a solution or mixture of a phospholipid, one or more hydrophobic drugs and a near critical fluid, wherein said near critical fluid is at a pressure between the critical pressure and 75% of the critical pressure of the composition of such fluid and at a temperature which is at least 75% of the critical temperature of the composition of such fluid, said fluid selected from the group of carbon dioxide, nitrous oxide, halocarbons, propane, ethylene and ethane; and, b) injecting said solution or mixture into an aqueous phase to form liposomes.

* * * * *